United States Patent [19]

Holmes et al.

[11] 4,138,878
[45] Feb. 13, 1979

[54] METHOD AND APPARATUS FOR DETECTING AND MEASURING SCALE

[75] Inventors: Elmond A. Holmes, Fullerton; Gilson H. Rohrback, Whittier, both of Calif.

[73] Assignee: Rohrback Corporation, Santa Fe Springs, Calif.

[21] Appl. No.: 747,426

[22] Filed: Dec. 3, 1976

[51] Int. Cl.² .......................................... G01N 25/00
[52] U.S. Cl. ...................... 73/15 R; 73/61.2
[58] Field of Search ............... 73/15 R, 61.2, 190 H, 73/204; 324/71 R

[56] References Cited

U.S. PATENT DOCUMENTS

| | | | |
|---|---|---|---|
| 2,264,968 | 12/1941 | DeForest | 73/15 |
| 2,330,599 | 9/1943 | Kuehni | 73/15 |
| 3,232,113 | 2/1966 | Malone | 73/190 |
| 3,246,515 | 4/1966 | Martino et al. | 73/204 |
| 3,286,174 | 11/1966 | Schaschl | 73/204 X |
| 3,326,040 | 6/1967 | Walsh | 73/204 |
| 3,392,575 | 7/1968 | Galler | 73/61.2 |
| 3,810,009 | 5/1974 | Hausler | 324/71 X |

*Primary Examiner*—Herbert Goldstein
*Attorney, Agent, or Firm*—Gausewitz, Carr & Rothenberg

[57] ABSTRACT

A thermal bridge is employed to compare thermal transfer characteristics of test and reference surfaces immersed in identical fluid environments so as to determine thermal transfer characteristics of the test surface substantially independent of fluid environment. The thermal bridge is balanced, the test surface is caused to be scaled to a greater degree than the reference surface and a comparative measurement is made with the two surfaces exposed to identical fluid environments. The method is performed by a single probe having two or more surfaces that are heated and of which the differential temperatures are monitored. Readings are adjusted to compensate for effects of a varying fluid environment.

49 Claims, 14 Drawing Figures

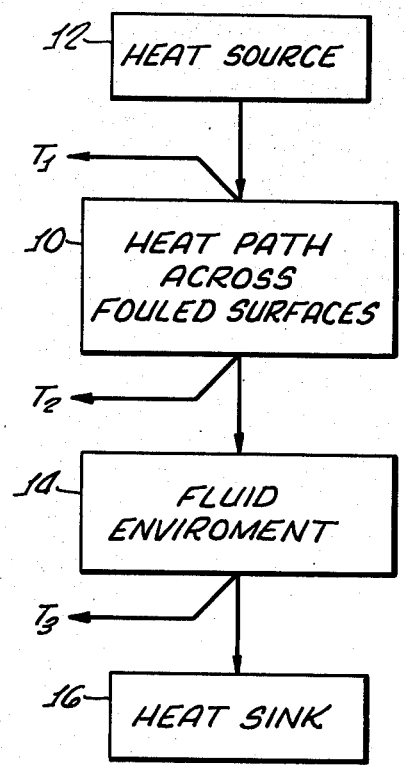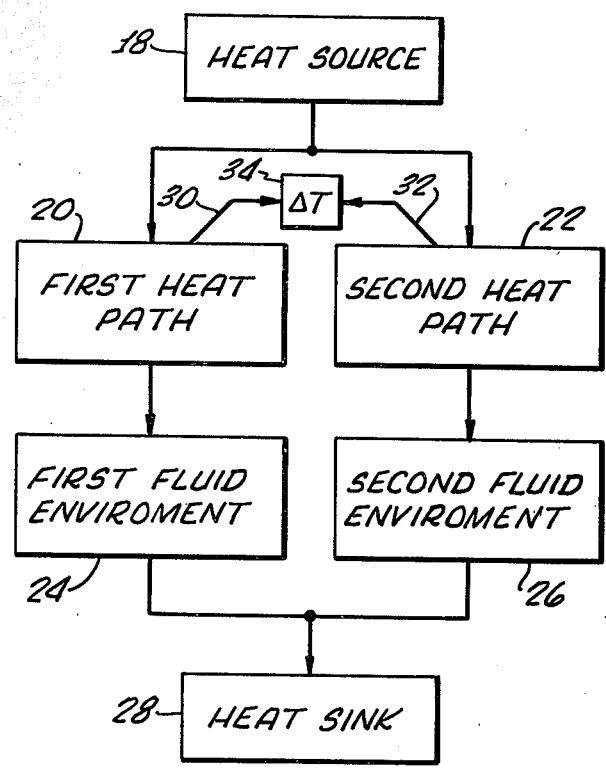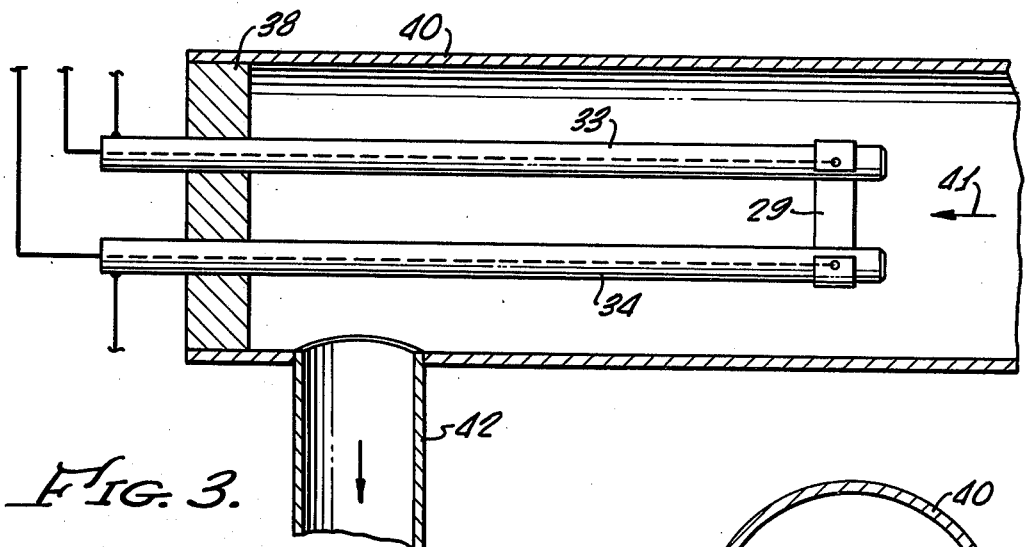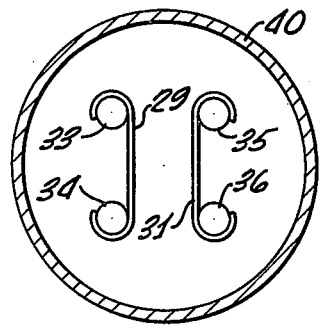

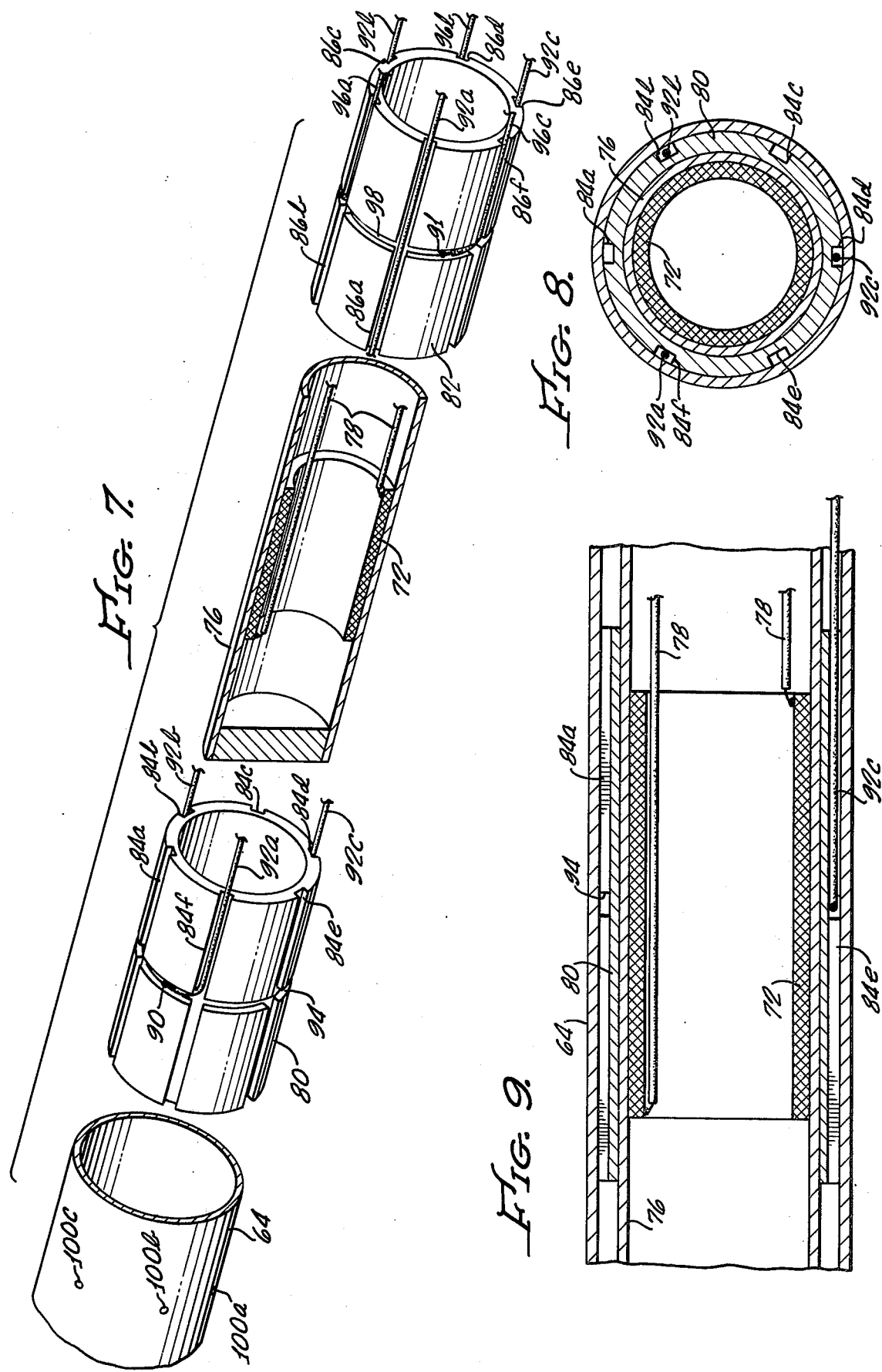

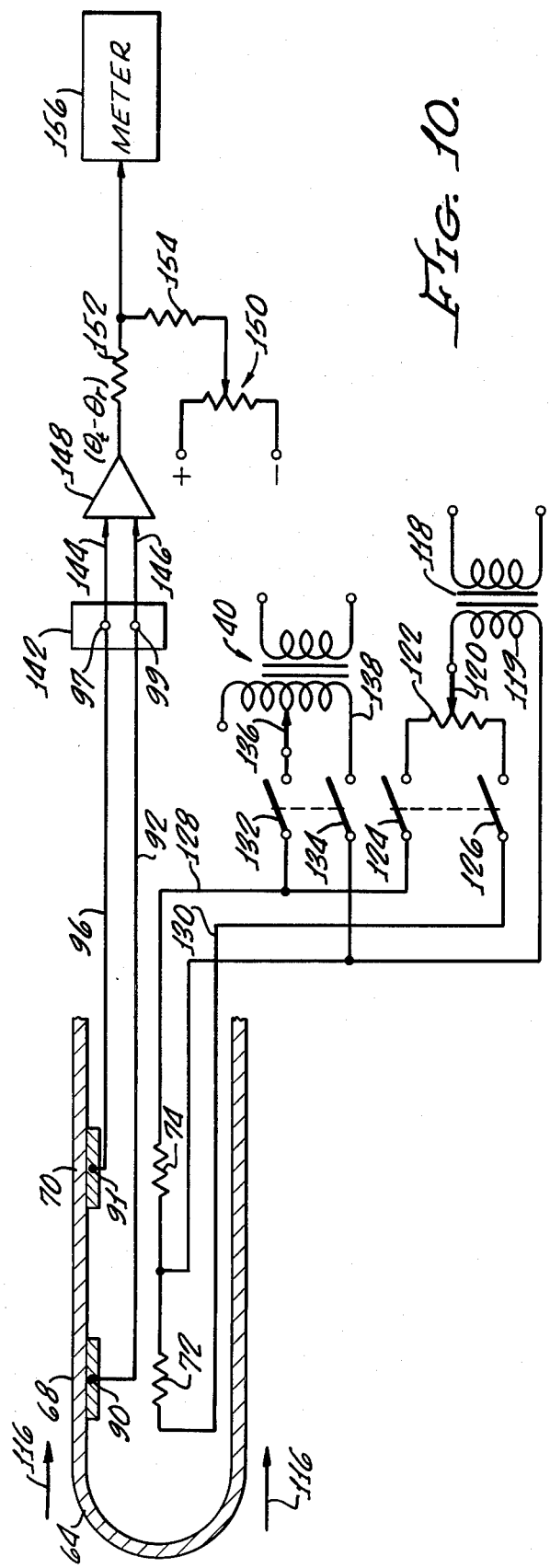
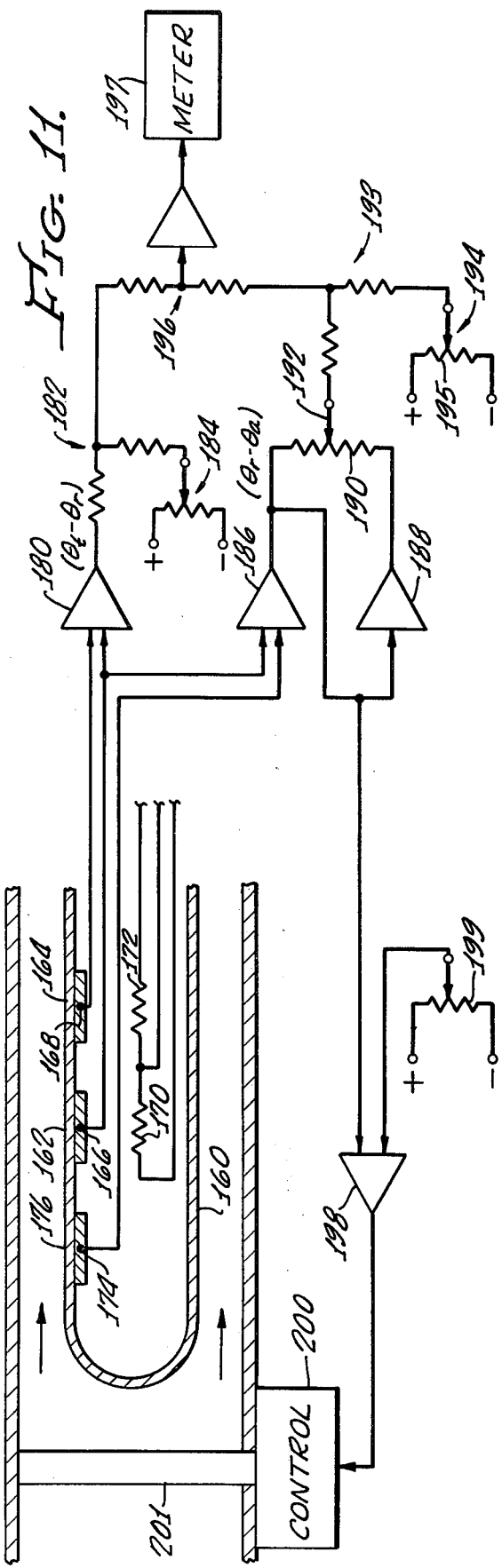

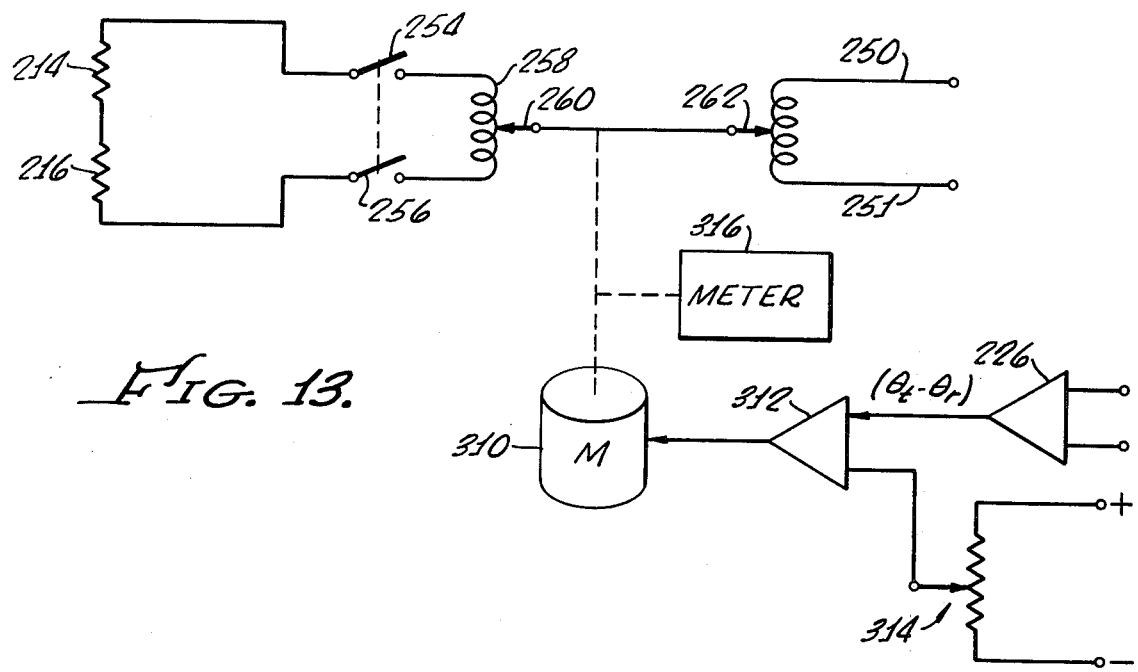
Fig. 13.
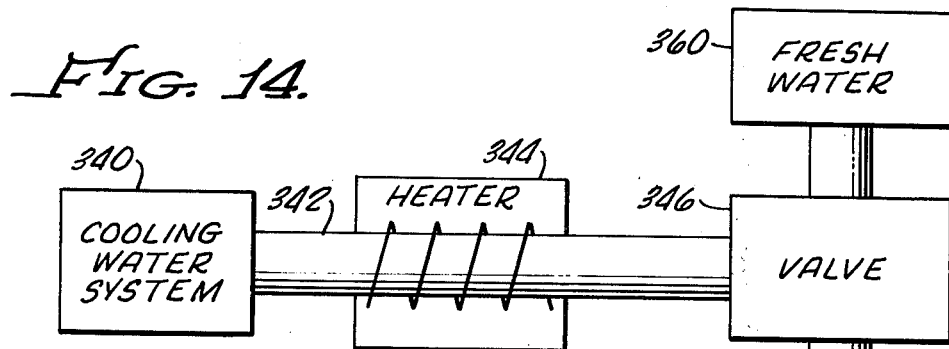
Fig. 14.
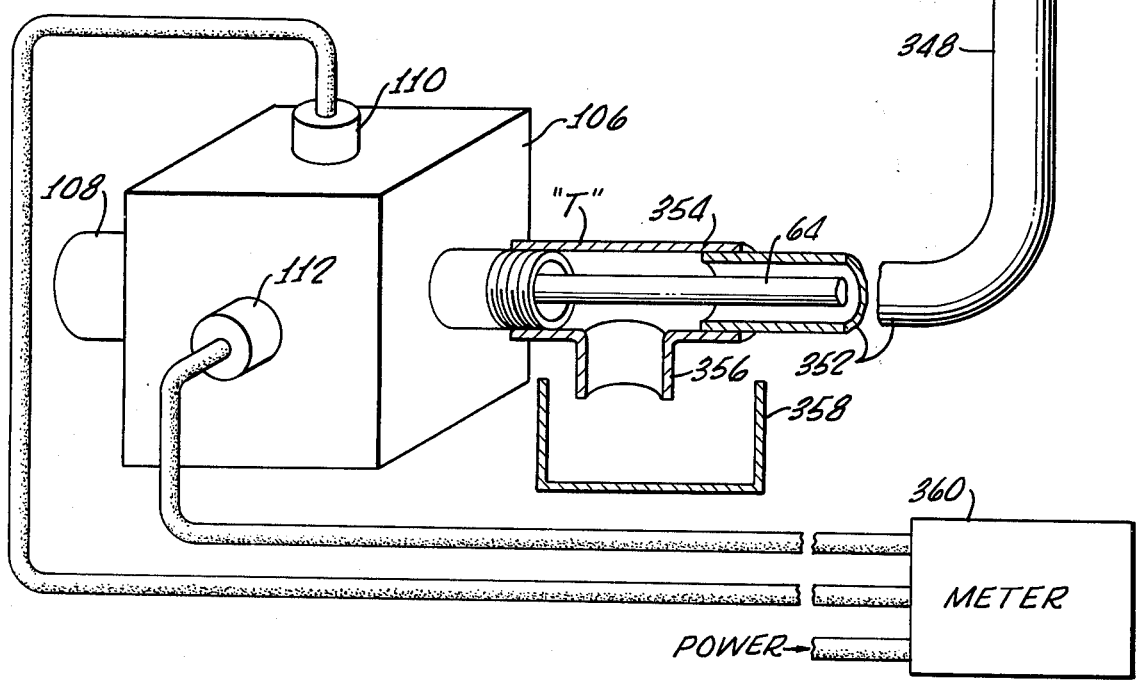

METHOD AND APPARATUS FOR DETECTING AND MEASURING SCALE

BACKGROUND OF THE INVENTION

This invention relates to detection, measurement and control of the formation of adherent precipitates such as scale, paraffin, wax, etc. on various surfaces.

The formation of aherent precipitates on equipment surfaces immersed in liquids is a long standing, widespread and costly problem in the industry. Such deposits reduce the rates of heat transfer, increase corrosion and erosion, clog flow lines and interfere with the proper functioning of instruments and control systems.

The most common form of such troublesome foulant coatings is adherent inorganic scale which often precipitates from water used in industrial equipment. For example, insoluble deposits of alkaline earth metal carbonates and sulfates frequently precipitate on the surfaces of heat exchanger tubes, thus reducing by major amounts the rates of heat transfer. The fact that the tubes are hot is a primary reason for such scale formation.

Although adherent inorganic scale is the most common form of foulant, it is emphasized that adherent organic deposits are also major problems in certain industries. Thus, the formation of harmful precipitates is not confined to aqueous systems. For example, in the refining of oil sticky adherent deposits form on metal surfaces of the reactors, heat exchangers or transfer lines. These deposits are often the result of heating of the oil being processed, which heating changes or decomposes asphaltic constituents, asphaltines or similar substances to form undesired adherent coatings. In other instances cooling, instead of heating, is the cause of the problem. For example, crude petroleum oil will deposit adherent coatings of paraffin wax when the temperature of the oil or of the surfaces over which it passes is lowered sufficiently.

Where a liquid is treated with chemicals to control corrosion, bacteria or other characteristics of the liquid, adherent scale derived from such chemicals may also be formed.

Scale or other deposited foulant coating is also a troublesome occurrence in many systems containing organic liquids. For example, deposits frequently occur in high wattage electrical transformers in which the windings are immersed in hydrocarbons or in halogenated aromatic compounds and the like; in hydraulic oil systems containing polyols, ethers and other organics; in heat transfer liquid systems such as heavy oil, bisphenol A or similar high boiling organics; and in numerous organic chemical processing units.

Scale and other harmful foulant coatings are likewise found in two-phase systems. For example, in the processing of freshly produced crude oil, the fluid is heated in a "heater-treater" unit to separate the unwanted salt water. Alkaline earth metal carbonates and sulfates are often present as adherent scale in such treating systems, the scale being sometimes mixed with various amounts of organic material.

There exists a major need for a practical, commercial method of determining whether or not a system is forming significant scale or other adherent precipitates, of determining the conditions under which scale might form, and of determining the conditions under which such formation can be prevented either by addition of chemical scale inhibitors or by control of process variables. It is highly important that the method be capable of implementation by commercial instruments, which function at all times and which do not require trained chemists or scientists for their operation. It is also extremely important that the method be so sensitive that the propensity of a system to develop scale will be detected without waiting until the foulant has created substantial harm in the commercial system being monitored.

In the past, physical inspection of plant equipment has been the common method of ascertaining the presence and existence of adherent scale and other precipitates. Another common method has been to measure changes in heat transfer rates (or in required liquid flow velocities to maintain a certain heat transfer rate). Both of these common methods suffer from the fatal deficiency that the harm which it is desired to prevent (for example, lowered heat transfer rate) must occur before "preventive" measures can be taken.

Because of the great difficulty of making physical inspections of the industrial equipment itself, one method of making heat exchanger studies is to specially design, construct and operate a laboratory model heat exchanger. Such a model usually includes windows for visual inspection, or includes means for withdrawing heat exchanger tubes so that they can be inspected and analyzed. Similarly, it is known to design laboratory heat exchangers wherein the heat transfer rates are monitored in relation to electrical power input, or steam condensation rates. Obviously, the construction and operation of such laboratory models is expensive and time-consuming and the data obtained with them may not be truly representative of what is occurring in the actual industrial equipment. Furthermore, reliance on changes in heat transfer rates, or on macroscopic inspection of surfaces, produces a fatal insensitivity.

In addition to constructing and operating models of heat exchangers or other industrial equipment, there are frequently employed, in the laboratory, chemical methods related to formation of scale and similar substances. For example, test solutions are prepared which are basically unstable and will, in response to heating or standing, and to the passage of time, yield precipitates of alkaline earth metal carbonates or sulfates. Different chemicals are added to such test solutions, and the degree to which such additives prevent or inhibit precipitation is determined. It is, however, emphasized that such tests do not provide continuous monitoring of an actual commercial system, nor do they necessarily produce significant data relative to formation of adherent scale in the actual system. It is to be noted that adherent scale or other precipitate is extremely harmful, but that those precipitates which are not adherent may be relatively harmless.

Other examples of laboratory procedures relative to scale, etc., involved determining the stability of the water in aqueous systems. Stability is ascertained by measuring or calculating from composition analysis, the minimum amount of acid or base required to effect precipitation. The amount of reagent tolerated by the solution without precipitation is taken as being proportional to stability and thus as being inversely proportional to the scale-forming tendency of the liquid. Such periodic tests can, at best, only be indirectly and uncertainty related to the tendence of an actual system to form adherent scale or other deposits.

In our prior U.S. Pat. Nos. 3,848,187 and 3,951,161, we describe extremely precise high sensitivity methods of employing electrical contact resistance to sense incipient precipitation of a foulant coating such as an adherent scale, paraffin wax or the like. The methods and apparatus described in these patents are useful, effective and of high sensitivity, but require moving parts that could adversely affect operation over long periods of time. Further, moving parts also add complexity and cost.

Detection and measurement of foulant coatings employing variations in heat transfer caused by a buildup of a foulant coating have been known in the past and avoid problems of moving parts. However, all of these methods lack sensitivity required for rapid and real time evaluation and, in addition, are subject to major errors due to various changes that may occur in the fluid during or between measurements.

In one such method, a test surface is heated electrically while monitoring the temperature of its surface that is in contact with the fluid. After a period of immersion in the fluid of which the foulant propensity is to be detected, temperature is again monitored and the temperature difference between the first and second measurements is employed as an indication of the change in foulant coating between the times of the first and second measurements. Prior methods employing this principle of detecting changes in heat transfer characteristics caused by changing foulant coatings, are useful as a practical matter only for detection of large changes in foulant coatings. By the time such a prior art system can provide a useful measurement, serious foulant deposit may have already occurred. Such systems are unable to measure relatively small changes in foulant coatings because the readings vary widely as sensitivity is increased. A problem with such prior systems is the fact that the measured temperature varies with many different parameters of the fluid in which the test surface is immersed. In some systems flow rate through a test cell is increased in order to stabilize cell temperature at the entering fluid temperature. With such high flow velocities, the flow velocity itself becomes most critical. Thus for an instrument of high sensitivity, relatively small variations in any one of a number of parameters of the fluid may cause an output reading to vary from zero to full scale even with only a slight disturbance in a parameter such as flow rate. Fluid parameters that affect this temperature measurement include fluid velocity, viscosity, temperature, composition, thermal conductivity, flow pattern at the surface (which may vary with varying roughness due to increasing foulant coating), and other flow patterns, among others. Therefore, with prior measurements based upon monitoring of changes in heat transfer due to changes in foulant coating, it is necessary to maintain all of these fluid parameters the same at each measuring period so that the fluid at the test surface has the same effect upon surface temperature at one measuring period as it does during a subsequent measuring period. Even under laboratory conditions, such identity of fluid characteristics is exceedingly difficult to achieve. In practical circumstances and in field situations, particularly where an instrument is to be used for long term monitoring of an actual system, control of such fluid characteristics is not feasible.

In summary, previous methods known for monitoring scaling, other than our prior U.S. Pat. Nos. 3,848,187 and 3,951,161, do not detect or measure accumulation of foulant in an actual system before such foulant has built up to a degree sufficient to cause significant damage, nor do such prior systems provide a way to test a particular liquid in order to determine in a relatively short time its foulant propensity.

Accordingly, it is an object of the present invention to detect and/or measure foulant or foulant propensity of a fluid before such foulant will adversely affect operation of a system. Another object of the present invention is the detection and measurement of foulant in a system by means of measurement of heat transfer characteristics and without the necessity of removing a test surface from the fluid in which it is immersed. Another object of the invention is to determine quickly and readily conditions under which foulant of various types will precipitate from various fluids.

SUMMARY OF THE INVENTION

In carrying out principles of the present invention in accordance with a preferred embodiment thereof, there is provided an unique thermal bridge in which a test surface is subjected to a fluid environment of which propensity to deposit foulant upon a surface immersed therein is to be detected or measured. Subsequently in a measuring period, both said test surface and a reference surface are subjected to fluid environments having a known relation of heat flow parameters, and heat transfers between both surfaces and their respective fluid environments are compared. Preferably, the fluid environments to which the test and reference surfaces are subjected have mutually identical heat transfer characteristics for simplicity of mechanization. According to a feature of the invention, the test and reference surfaces are initially thermally adjusted by applying thereto a differential heat input that causes the indicated relative heat transfer characteristics to exhibit a minimum change over a range of variations of the fluid environment. According to another feature of the invention, improved insensitivity to variation of fluid environment during a measuring period, even at very high levels of measurement sensitivity, is achieved by compensating the output indication according to a selected function of sensed variations in the fluid environment, and/or by controlling the fluid environment at the test and reference surfaces so as to decrease such variations.

The present invention, having no moving parts, and being relatively insensitive to variations in fluid environment, is readily embodied in a simple probe that may be exposed to actual fluid of a system to be monitored so as to provide either intermittent or continuous readout and record of foulant or foulant propensity with such a sensitivity as to signal said adverse fouling before the monitored system is damaged by fouling.

BRIEF DESCRIPTION OF THE DRAWINGS

FIG. 1 is a diagram illustrating a single path heat transfer measurement of prior art;

FIG. 2 is a functional diagram of a thermal bridge employed in carrying out principles of the present invention;

FIG. 3 is a side view of a simple mechanization of principles of the present invention;

FIG. 4 is an end view of the instrument of FIG. 3;

FIG. 7 is an exploded perspective view, with parts broken away, illustrating components of the probe of FIG. 6;

FIG. 8 is a section taken on line 8-8 of FIG. 6;

FIG. 9 is an enlarged fragmentary longitudinal section of the probe of FIG. 6;

FIG. 10 is a diagram of electrical circuits used in conjunction with the probe of FIGS. 6-9;

FIG. 11 is a diagram of other electrical circuits that may be used with the probe of FIGS. 6-9;

FIG. 13 shows a modified heating circuit for the probe of FIGS. 6-9; and

FIG. 14 illustrates a typical application of a scale sensitive probe to an exemplary fluid system.

DETAILED DESCRIPTION

Figure 5:
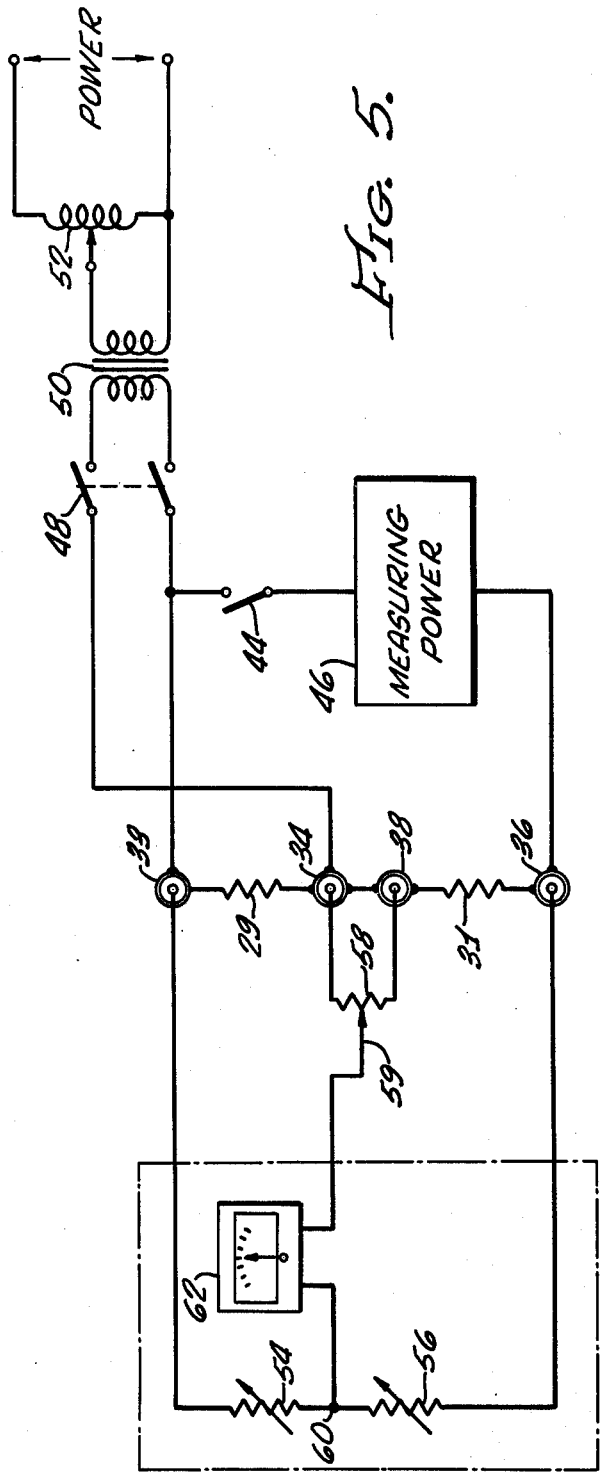
FIG. 5 is an electrical circuit diagram of the instrument of FIGS. 3 and 4.

The present invention derives significant advantages from use of an unique thermal bridge to detect or measure foulant coating by means of its heat transfer characteristics. In order to fully appreciate advantages derived from this type of measurement, there will first be described aspects of prior art arrangements that attempt to measure foulant by means of heat transfer characteristics.

It is known that deposited scale and other foulant form a coating on a surface that changes its heat transfer characteristics. Thus, if one heats the surface and measures the heat transfer from the surface to a fluid in contact with the surface, one can, theoretically, obtain an indication of the foulant coating in terms of change in the heat transfer characteristic of the surface. Such a previously known arrangement is functionally illustrated in FIG. 1 wherein a foulant coated surface represented by box 10 is heated from a heat source 12.

Box 10 represents part of a foulant test element heated at one side by heat source 12 and having its other side in contact with a fluid environment 14. A temperature sensing device is positioned within the foulant test element at a point $T_1$. Thus box 10 represents only those parts of the foulant test element between the point $T_1$ and the fluid environment. Other parts of the foulant test element between point $T_1$ and the heat source may be treated as part of the heat source, for purpose of this discussion. Heat flux flows across the fouled surface (and across the foulant coating thereon) and thence into fluid environment 14 that is in contact with the surface. Heat flux flowing into the fluid is carried away as indicated by a line showing flow of the heat flux from the fluid environment into a heat sink 16. The heat sink may represent the fact that fluid is flowing past the surface 10. If it were possible to measure temperature at both sides of the heat path across the fouled surface, at points such as $T_1$ and $T_2$, one could obtain a measure of the heat transfer coefficient across or through the heat path 10, which includes the fouled surface. $T_2$ is the surface of the test element (or of the foulant coating upon the fouled test element) in contact with the fluid.

Temperature $T_2$ is not readily measured by any known method since the interface of foulant and fluid varies as foulant is deposited. The temperature $T_3$ of heat sink 16 (which is the temperature of the fluid environment at the heat sink) must be measured instead. The temperature difference between $T_1$ and $T_3$ is caused by the heat flux not only in the heat path across fouled surface 10 but also by heat flux across fluid environment 14.

It will be readily observed that the temperature drop across the fouled surface through the path 10 and across the fluid environment through path 14 depends upon the thermal resistance of path 14 as well as of path 10.

With all other conditions constant, the temperature at $T_1$ will have a relatively lower value when thermal characteristics of fluid environment 14 are such as to cause a small temperature drop $T_2 - T_3$. On the other hand, temperature $T_1$ will have a higher value when the fluid environment thermal characteristics are such as to cause a larger temperature drop $T_2 - T_3$.

The temperature drop due to the heat flux that will flow into the fluid environment and to the heat sink is a function of a great many thermal characteristics or parameters of the fluid chemistry and hydrodynamics. Such parameters include flow velocity, the pattern (turbulence) of flow, surface texture, fluid viscosity, fluid temperature, and fluid composition, among others. All of these parameters are included in the term "fluid environment" as used throughout this application. Thus it may be seen that for a given and unvarying heat source 12, and a given and unvarying fouled surface 10, the temperature $T_1$ may vary widely as parameters of the fluid vary. Therefore, according to prior concepts, if any useful measurement of heat transfer coefficient in such a situation is to be made the fluid environment (e.g. the fluid and all of its temperature affecting parameters) must be constant during a given measurement and, in addition, must be either exactly the same from one measurement to the next or have such known variations as to enable compensation of the heat transfer reading for such variations. However, adequately precise control of fluid environment is difficult at best and impossible under many circumstances, including field conditions.

THERMAL BRIDGE

According to a feature of applicants' invention, heat transfer characteristics of a foulant coated surface are readily detected or measured without necessity of precision control of fluid environment. According to this feature of applicant's invention, there is provided a novel form of thermal bridge, in some respects analogous to an electrical bridge (such as a Wheatstone bridge), in which heat flux is caused to flow through first and second heat paths, across first and second surfaces, to first and second fluid environments. The two fluid environments are constrained to have a fixed relation of heat transfer characteristics. This fixed relation is most readily achieved by use of substantially identical fluid environments. Now, rather than merely measure temperature at a single surface, across a single heat path, one merely observes the difference in temperature between similar locations in each of the heat paths, in effect comparing or differentially measuring the temperature drop through the first and second heat paths and the first and second fluid environments. Differences in thermal resistivities of the two heat paths caused by differences in foulant coatings, for example, will be readily indicated by such comparison.

In the use of this thermal bridge it is not necessary to maintain the same (or known relation of) fluid parameters from one measurement to the next. It is only necessary to maintain the same relative parameters of the two fluid environments at the time of measurement. Within certain ranges these parameters may vary from one measurement to the next without seriously affecting the detection or measurement.

A thermal bridge according to this feature of the present invention is functionally illustrated in FIG. 2 wherein a heat source 18 generates heat flux that flows through first and second heat paths 20, 22, each of which includes a surface in contact with a respective one of two fluid environments 24, 26, which dissipate heat into a heat sink schematically indicated at 28. As previously indicated, the heat sink in this schematic illustration, may be, in effect, the fluid itself which may continually flow past the surfaces during measurement. Heat paths 20 and 22 include those portions of first and second fouling measurement elements (test and reference elements) between the fluid environment 24 or 26 in contact therewith and points 30 and 32 within the measurement elements. Temperature sensing devices are located at points 30 and 32. Portions of the fouling measurement elements between points 30 and 32 and the heat source 18 may be treated as part of the heat source for purposes of this discussion.

Heat flux from source 18 may be caused to flow to paths 20 and 22 in a predetermined relation for certain purposes, such as compensation for asymmetry of the paths as will be described below. However, for purposes of this discussion, it will be assumed that heat flux flows with equal flux densities through paths 20 and 22 from a constant heat flux source 18 and, therefore, that the relative temperature drop through the two paths is governed by their relative thermal resistivities.

It is also assumed for the purposes of this discussion that there is no thermal conduction between the two paths. Thermal resistance other than that of the first heat path 20 and first fluid environment 24 may be disregarded in one leg of this thermal bridge. Similarly, thermal resistance other than that of the second heat path 22 and the second fluid environment 26 may be disregarded in the second leg of this thermal bridge.

In the bridge of FIG. 2, as long as the first and second fluid environments 24 and 26 have heat transfer characteristics in a fixed relation to one another (or, in a specific case, the two fluid environments are identical to one another in thermal resistivity), it does not matter how the two vary, provided only that they vary in a like manner. In other words, it is only necessary, for use of this thermal bridge, that the relative effective thermal transfer characteristics of the two fluid environments remain constant from one measurement to the next, but the thermal characteristics may vary. This condition is relatively easy to obtain, particularly in two adjacent parts of the same fluid system.

With the relative effective thermal transfer characteristics of the two fluid environments 24 and 26 constant, the difference in temperature at points 30 and 32 is an accurate indication of the temperature drop through path 22 relative to the temperature drop through path 20. If the two paths have the same thermal resistance, or the same specific thermal conductivity (e.g. coefficient of thermal conduction), the temperature difference between points 30 and 32, as indicated in a meter 34, will be zero (assuming equal heat fluxes to the two parts 20, 22 from source 18). On the other hand, should there be a difference in thermal resistivities of the two paths 20 and 22, as caused for example by a differential coating (one surface being more fouled than the other), then (with equal heat flux inputs) there will be a difference in temperature drop through the first and second paths. This difference depends upon the difference in thermal resistivities of the two paths, which in turn depends upon the difference in foulant coating of the two. The difference is indicated on a meter 34 which reads in terms of difference in temperature ($\Delta T$) at points 30 and 32.

This difference is independent of variations of fluid environment, assuming symmetry of the surfaces and ideal instrumentation. However, at very high sensitivities, asymmetries and instrumentation errors may cause changes in fluid environment to affect the measurement. Described below are methods and circuits to compensate for such effects to thereby provide still further increase in sensitivity.

The above-described thermal bridge may be employed in many different forms to practice the present invention. In general, a test element which provides a heat path analogous to heat path 20, for example, of FIG. 2, has a surface thereof immersed in a fluid of which the foulant propensity is to be determined. This surface is allowed to remain so immersed for such time and under such conditions as to normally have some degree of foulant coating deposited thereon by the fluid in which it is immersed. Thereafter the described thermal bridge is employed to measure or detect the foulant coating, if any, that the surface has acquired. For such measurement or detection, the test surface and a surface of a second element, which may be termed a reference element (and which is analogous to heat path 22), are both immersed in substantially identical fluid environments (or fluid environments having known relative heat transfer characteristics). The reference surface has no foulant at the time of measurement. The test and reference elements have a known relation (such as identity or near identity) of heat transfer characteristics prior to exposure of the test surface to the possibly foulant environment. While immersed, both surfaces are heated by source 18 for a measurement. The relative heat transfer through paths 20 and 22, or more specifically, across the interface between the test surface and its fluid environment, on the one hand, and the reference surface and its fluid environment on the other hand, are compared. This comparison provides the desired indication of test surface foulant.

Such a method, without additional steps will provide a detection and measure of foulant on the test surface as compared to the reference surface. For detection or measurement, the thermal bridge is initially adjusted, preferably when both the test and reference surfaces are in a like condition (a clean and unfouled condition, for example) so that in such like condition indicator 34 provides a first known reading (such as a null). After a foulant period in which the test surface has been exposed to potentially foulant conditions (whereas the reference surface has not been so exposed, or has been exposed to a lesser degree, or has been cleaned, or has been otherwise protected from foulant), the differential measurement is repeated, observing the difference indicated by meter 34. The difference between the reading of the meter 34 at the measurement period and its reading at the initial measurement period, is an indication of the change in thermal transfer characteristics of the test surface subsequent to the period at which the bridge was initially adjusted. Thus the reading is a measure of foulant.

RESISTANCE HEATED PROBE

Illustrated in FIGS. 3, 4 and 5 is a simplified apparatus employing principles of the above-described thermal bridge and useful for detection of foulant. A test element 29 and an identical reference element 31 are fixedly carried at the ends of respective pairs of hollow support posts 33, 34, and 35, 36, which are fixedly mounted in an end cap 38 of an elongated probe housing 40. Probe housing 40 has an inlet (not shown) through which there is fed a fluid, flowing in the direction of arrow 41, of which the foulant propensity is to be measured. The fluid preferably flows in the same undisturbed flow pattern over the test and reference elements 29, 31 and thence through an exit conduit 42. In this simplified arrangement, the test and reference elements each are formed of a thin ribbon of electrically conductive temperature sensitive material, such as nickel or platinum, in which the temperature coefficient of resistance is sufficiently large to provide a measure of temperature of the surfaces which are exposed to the fluid. The temperature sensitive ribbons 29, 31 are connected for measurement by insulated electrical leads which pass through the electrically conductive hollow supporting posts 33-36 out from the probe for connection to an electrical circuit illustrated in FIG. 5.

The ribbons are connected for heating by current flowing through the ribbons from the posts. The ribbons are connected in series via posts 33-36 and a measuring switch 44 to a source of electrical measuring power 46 sufficient to heat both of the ribbons to a temperature selected for use during a measuring period. The test ribbon 29, but not the reference ribbon 31, is connected, via posts 33, 34, to a source of "foulant" electrical power by means of a foulant switch 48, a coupling transformer 50 and a variac or variable transformer 52. For measurement, the two resistive ribbons are connected (via the leads extending through the posts) in an electrical bridge circuit including variable resistors 54, 56 which are connected in series to each other and have their opposite ends respectively connected to one end of each ribbon. The other end of each ribbon is connected to opposite ends of a resistor 58 having a center tap 59. The output of the bridge, at tap 59 and at junction 60, between resistors 54 and 56, is fed to a meter 62 which accordingly will display a quantity representing the difference in temperature of the test and reference ribbons 29, 31.

In operation of the probe of FIGS. 3, 4 and 5, the fluid under observation is caused to flow through the probe housing 40 while the instrument is adjusted. Adjustment is made with the ribbons in clean, unfouled condition. Power switch 48 is open and measuring switch 44 is closed to provide AC or DC heating current equally through both of the ribbons in the series connected measuring circuit. This heating current is a measuring current that is chosen to be of a magnitude that will raise the temperature of the test and reference elements above the temperature of the surrounding fluid. The temperature rise (above the fluid temperature) is chosen for optimum sensitivity of element resistance change to accumulated foulant. A higher temperature rise will provide a greater sensitivity. However, the temperature must be below the boiling point of any phase of the fluid and below any temperature that would cause a chemical reaction. In general, a 10° to 20° Fahrenheit temperature rise is useful for many systems.

During this measuring period (e.g. during application of measuring current), one or both of resistors 54, 56 of the electrical bridge are adjusted to provide a null (or other known) reading of the meter 62. Then the measuring switch 44 is opened to remove the measuring current and a foulant period is commenced. During this foulant period the test surface 29 is exposed to a fluid environment of enhanced foulant propensity as compared to the foulant propensity of the environment to which the reference surface 31 is exposed. In the illustrated probe, the relative enhancement of foulant propensity of the environment of test surface 29 is achieved simply by heating only the test surface, while causing the reference surface to remain at the lower temperature of ambient fluid. The test surface is heated by closing foulant switch 48 to provide a selected amount of heating (foulant inducing) current flowing solely through ribbon 29 but not through ribbon 31. Increasing surface temperature increases the rate of deposition of foulant or the probability that foulant will be deposited. The heating current for the foulant period is chosen to have a magnitude sufficient to cause the desired surface temperature (of test ribbon 29) at which the fouling propensity of the fluid is to be determined. This temperature may be varied from one measurement to the next to enable study of different fouling conditions of a system. Test surface temperature may be separately measured by means (not shown) if deemed necessary or desirable to verify the temperature of the test surface during the fouling period. Other parameters of the fluid environment may also be controlled during the foulant period to permit study of their foulant effects.

After a period of time, during which the test surface may or may not have accumulated or begun to accumulate a foulant deposit under the selected conditions, the foulant switch 48 is opened and a measurement period is initiated. The measuring switch 44 is again closed and temperature difference is read.

The fluid environment is stabilized during the measuring period, but not necessarily at the same parameters as in the foulant period or in a prior measuring period.

During the measuring period, with measuring power applied to the ribbons 29 and 31, the apparatus operates in the manner described for operation of the thermal bridge of FIG. 2. The heat source in this case is resistance heating applied equally to both the test and reference elements. The heat paths of the two bridge legs, analogous to paths 20 and 22 of FIG. 2, extend through the ribbons and across the interface between each ribbon and the fluid environment. The latter flows with substantially identical thermal transfer characteristics past both of the surfaces for discharge via conduit 42. Because of the high temperature coefficient of resistance of the material of ribbons 29 and 31, their resistances are related to their temperatures. Therefore, the bridge outputs at points 59 and 60, which produce an electrical signal indicative of the difference of the resistances of elements 29 and 31, provides a readout indicative of the temperature difference of these elements. Since this difference was balanced or nulled out initially, any change observed during the second measurement, from the position noted at the first or adjusting measurement, is an indication of change of temperature difference and thus indicates that one surface is more fouled than the other.

Assume that test surface 29, which was heated to a selected foulant temperature during the foulant period, has acquired a foulant coating, and reference surface 31, which remained at the temperature of the fluid environment during the fouling period, has acquired no foulant coating. Then, as described above in connection with the discussion of the thermal bridge, the same heat input to each of the two elements which are in contact with substantially identical fluid environments, will result in higher temperature at the test surface than at the non-coated reference surface.

In effect, the temperature measurement is made internally of the foulant coated test element, or at least inwardly of the foulant coating. The latter acts as a heat insulator between the heated test element and the cooler fluid. Thus the fouled test element will exhibit a higher temperature than the non-fouled reference element.

The temperature difference between test and reference elements is an indication of the existence of foulant on the surface 29 and is observed as a change in the reading of meter 62 from one measurement period to the next.

The measuring period may be from 5 to 15 minutes in length, requiring a duration sufficient only to allow the circuit to stabilize, thermally and electrically, as its heat input is changed from one condition to another. A typical foulant period (e.g. time between two successive measuring periods) may be in the order of 1 to 4 hours. Cyclic alternation of measurement and foulant periods is continued as long as observation of the fluid system is desired.

The methods and apparatus described above, and also those described hereinafter, may be used to rapidly determine conditions under which adherent foulant is precipitated. It is only necessary to select a given condition during the foulant period and to measure foulant effects thereof during a subsequent measurement period. For example, by selecting the heat applied to the test surface, or the temperature, composition or viscosity of the tested fluid during the foulant period, foulant effects of such specific conditions can be individually studied.

The apparatus illustrated in FIGS. 3, 4 and 5, although illustrative of one mechanization of the thermal bridge of FIG. 2, is a simplified device which, without addition of further compensation circuits, is adapted for precise and rapid detection or gualitative indication of foulant rather than measurement or quantitative indication. Embodients of foulant probes and circuitry capable of achieving precise, rapid and quantitative measurement are described below.

It will be readily understood that principles of the present invention may be embodied in many different mechanisms and different circuits which will perform the functions of the above-described thermal bridge. A wide variety of heat sources may be employed, including various arrangements of separate internal or external heaters, whether electrical or fluid (such as steam) and direct resistive heating. A wide variety of temperature sensing may be employed, including various sensing devices independent of the heating devices, such as thermistors, thermocouples and the like.

Many methods of achieving differential fouling of the test and reference surfaces may be employed. Our prior U.S. Pat. Nos. 3,848,187 and 3,951,161 describe a number of such methods of enhancing foulant tendency, thereby to significantly increase the rate of fouling or potential fouling and thus effectively increase sensitivity of the measurement. Such methods are readily employed to differentially foul the test and reference surface (thus causing a greater fouling or a greater likelihood of fouling of the test surface than the reference surface). Methods of differentially fouling include physical protection of the reference surface while the test surface is exposed to foulant conditions. Thus the reference surface may be detachable or separate from the test surface and removed from the fluid environment during the foulant period. The reference surface may be exposed to foulant conditions with the test surface but cleaned prior to a subsequent measurement (after the foulant period). The reference may be provided with a protective coating. Chemical inhibitors may be employed, confined to an area immediately adjacent the reference surface. For those fluid systems where fouling is enhanced by lower temperatures, cooling devices may be employed to lower the temperature of the test surface below that of the fluid environment, while maintaining a higher temperature of the reference surface, or otherwise protecting the latter from foulant.

Still another method of attaining differential fouling is the application of equal heating power to the reference and test surfaces during the fouling but employing a lower fluid temperature around the reference surface. Then during a measurement period fluid flow is increased or other steps are taken to equalize the fluid environment at the reference and test surfaces.

Various arrangements of differentially heating the reference and test surface may be employed to obtain differential fouling of test and reference surfaces during the foulant period. Both test and reference surface may be heated but with a heat input to the test surface of several times the heat input to the reference surface.

INTERNALLY HEATED EXTERNAL FLOW PROBE

Test probe construction and configuration may vary widely without departing from principles of this invention. In addition to different arrangements of heating and temperature sensing, probes may be built to allow fluid under test to flow either internally or externally of the probe. The latter configuration is selected for exposition of further aspects of this invention. The external surface probe is preferred because it is more readily inspected and more readily cleaned mechanically.

Figure 6:
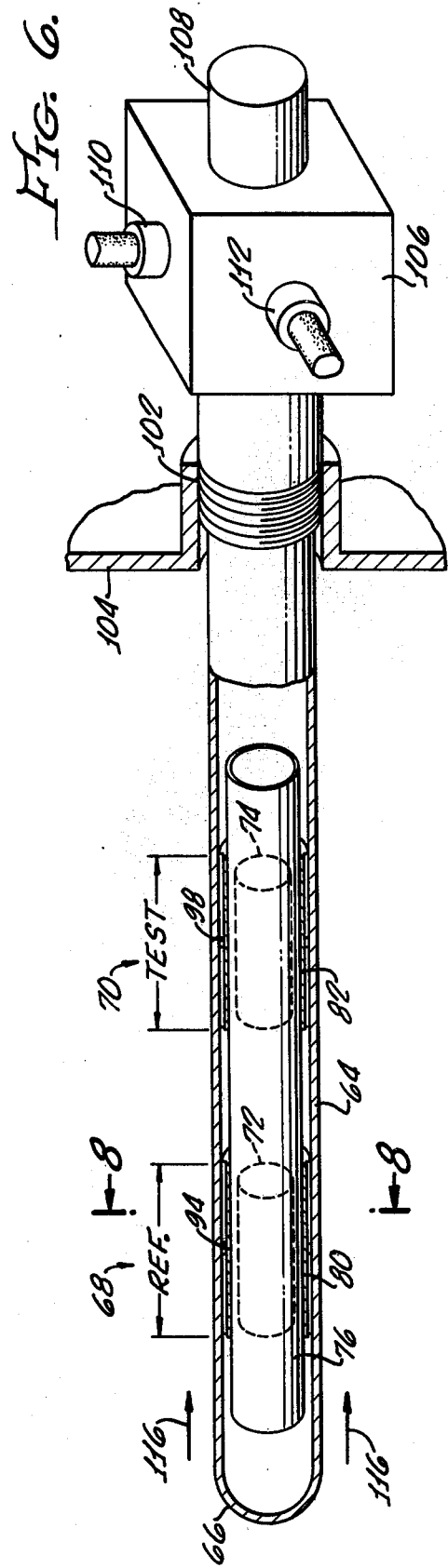
FIG. 6 is a sectional view of a probe embodying principles of the present invention.

Illustrated in FIG. 6 is an embodiment of the invention presently preferred for certain types of aqueous systems such as cooling water systems, although this probe may be used with many other types of systems. The probe of FIG. 6 is particularly adapted for use with various adjustment and compensation circuitry, to be described below, which enables this instrument to provide quantitative measurements with an exceedingly high degree of sensitivity and accuracy.

Referring to FIGS. 6, 7, 8 and 9, a probe sheath 64 is formed of an elongated hollow tube of a thin walled heat conductive material, such as stainless steel, streamlined at an upstream or inboard end 66 thereof to minimize flow disturbance, and having a sufficient length to axially space its test and reference heaters and temperature sensors. An annular circumferential area of sheath 64, indicated at 68, is employed as a reference surface and a similar annular circumferential area, indicated at 70 and axially spaced downstream from area 68, is employed as the test surface. Mounted within the sheath 64 in fixed relation thereto is an electrical cartridge heater which may be of the type disclosed in U.S. Pat. No. 2,831,951, having mutually spaced and independently energized resistance heated wire coils 72, 74 mounted within a cylindrical metallic tube 76. Heater current leads 78 connect the heater coils to external heater power circuits to be described below.

To implement the concepts of the thermal bridge illustrated in FIG. 2, in the embodiment of FIGS. 6, 7, 8 and 9, it is desired to measure the difference in temperature between the reference surface 68 and the test surface 70. As previously mentioned, many different types of temperature sensing may be employed. Thus one may secure conventional thermocouples, thermistors or other temperature sensitive devices to the test and reference surfaces at interior or exterior thereof, or even within the heater cartridge itself, to provide the desired measurement of temperature difference.

It wil be recalled that the measurement achieved by the described thermal bridge does not require measurement of temperature at a given point, but merely requires measurement of a temperature difference. Since only a temperature difference is being measured, one can measure such difference at surfaces 68 and 70 simply by connecting a single thermoelectric thermocouple wire to each of these surfaces, that is, one wire to surface 68 and another wire to surface 70, provided that such wires are thermoelectrically different than the material of the electrically conductive sheath of the probe. When there is a temperature difference between areas 68 and 70, there is a thermoelectrically generated voltage gradient along the probe between these areas. Therefore, a voltage difference appearing across the two wires connected to the test and reference areas respectively, is a measure of such temperature difference.

Connection of such thermoelectrically dissimilar (relative to the probe sheath, not relative to each other) thermocouple wires to the exterior of the probe sheath or connection of other temperature sensing elements to the exterior of the probe sheath, is undesirable since patterns of flow over the exterior of the sheath may be disturbed and the probe becomes more difficult to clean. The probe embodiment described in FIGS. 6, 7, 8 and 9 measures difference in temperature at the test and reference surfaces by connection of thermoelectric wires to the interior of the probe sheath. The arrangement of the disclosed embodiment for connecting the thermoelectrically dissimilar wires in this embodiment also provides a good thermal path, a path of low thermal resistivity, from the heaters to the test and reference surfaces respectively and to the thermoelectrically dissimilar connecting wires.

For connecting the thermocouple wires, first and second heat conductive spacer sleever 80, 82 are mounted upon heater tube 76, over the respective heater coils. These sleeves are a tight press fit upon the heater tube and a snug, firm fit with the interior of the probe sheath. The sleeves may be made of a 1020-1040 mild steel, copper, or other material having good thermal conductivity and thermoelectric characteristics different than the material of the thermocouple wires. All thermocouple wires are of the same material, such as constantan, for example.

As can be seen in FIGS. 7 and 8, each sleeve has a plurality of circumferentially spaced longitudinally extending grooves or slots formed therein which cooperate with the probe sheath 64 to provide a plurality of passages or conduits extending longitudinally of the sleeves. The grooves of sleeve 82 are designated by numerals 84a, 84b, 84c, 84d, 84e, 84f, and similar longitudinal grooves 86a, 86b, 86c, 86d, 86e, 86f are formed in sleeve 82. For sensing temperature difference of the probe reference and test surfaces, thermoelectric (thermocouple) wires are fixed to the sleeves. Sleeve 80 has fixed thereto a plurality of electrically insulated thermocouple wires, such as constantan (for example) wires 92a, 92b, 92c, having uninsulated tips, such as tip 90, fixed to the sleeve, at points circumferentially spaced about the sleeve. Sleeve 82 is provided with a similar group of insulated thermocouple wires having uninsulated tips such as tip 91 fixed to the sleeve at circumferentially spaced points.

The wires have their tips secured, as by welding or brazing, to each sleeve in spaced circumferential relation with respect to each other to provide temperature difference sensing at spaced points about the peripheries of the test and reference surfaces. Thus, in the illustrated embodiment, three thermocouple junctions are provided at each sleeve. For each sleeve, the ends of its three thermocouple wires remote from the sleeve are electrically and thermally connected to each other, as described below, to provide a temperature difference that is the difference of an average of temperatures at circumferentially spaced parts of the test and reference areas.

Only one thermoelectric wire for each sleeve need be used, although a plurality (two, three or more) of such wires for each sleeve is preferred for averaging. For improved securement of the bare tips of the thermocouple wires to the sleeves 80, 82, the latter are provided with circumferentially extending slots 94, 98, respectively. Each thermocouple wire lies in one of the longitudinally extending slots of the sleeve and has its end bent around the corner formed by the intersection of such longitudinal slot and the circumferential slot, to be spot-welded to the sleeve within the circumferential slot. The three thermocouple wires of each sleeve are placed in alternate longitudinal slots. Thus wires 92a, 92b and 92c of sleeve 80 are in slots 84f, 84b, and 84d of sleeve 80. The intermediate slots 84a, 84c, 84e of the six slots of this sleeve remain unoccupied (FIG. 8). Actually, these additional unoccupied slots of sleeve 80 are not needed for wire passages and may be omitted. Nevertheless, all six slots are needed for wire passages of sleeve 82 and it is desired to make the two sleeves identical to attain as much thermal symmetry as possible, for reasons to be described below. Sleeve 82, which is identical to the sleeve 80, also has three electrically insulated constantan thermocouple wires 96a, 96b and 96c lying in alternate ones of its six slots and having their bare ends bent around into circumferential slot 98 and welded thereto (as at 91 for wire 96c).

Since all of the thermocouple wires are passed from the probe at the same end, the three thermocouple wires of sleeve 80, adjacent the reference surface of the probe, not only lie in the alternate slots of such sleeve, but also pass along the full length of those alternate slots of the test surface area sleeve 82 which are not occupied by the wires 96a, 96b, and 96c of the test area sleeve. Where temperature is to be sensed or compared at other (more than two) longitudinal positions along the probe, as described below, additional sleeves and thermoelectric wire junctions are provided at such positions, similar to sleeves 80, 82 and the junctions thereof. Wires of such additional sleeves may be passed out of the probe along additional slots (not shown) in those sleeves closer to the end of the probe at which the wires exit.

To enhance conduction of heat to the sleeves (and to the thermoelectric wires connected thereto) from the outer surface of the probe sheath, the sheath is provided with a plurality of circumferentially spaced holes such as holes 100a, 100b, and 100c. In the described arrangement, the effective thermocouple junctions at test and reference surfaces are between the steel sheath and the constantan wires although the mechanical junctions are between the wires and the sleeves (which are in good thermal contact with the sheath and form a part of the thermoelectric circuit.) The holes are positioned in registry with areas of the underlying sleeves displaced from the grooves therein. After assembly, these holes may be used to feed brazing material to sweat join the sleeve and outer sheath. Alternatively the holes may be omitted and brazing compound placed in the grooves before assembly of the sleeves to the sheath. Subsequent heating will cause the brazing compound to flow into spaces between the sheath and sleeve. If deemed necessary or desirable to still further improve heat transfer from the outer surface of sheath 64 to the measuring thermocouple junction, the sheath is swaged upon and against the spacer sleeves, ensuring that this swaging is performed without significantly disturbing the desired flow shaping characteristics of the smooth and unbroken outer surfaces of the sheath. Preferably, the swaging of the sheath upon the sleeve is performed before the brazing.

Thus it will be seen that the cartridge heater with its two separate heater coils is fixed to the two spacer sleeves, which are a press fit thereon, and that the sleeves are swaged, and/or may also be brazed, to and within the probe sheath to thereby provide a rigid, fixed unitary probe, having no moving parts. The heater 72 and thermoelectric wire junctions of the reference surface are symmetrically disposed internally of and circumferentially about the annular reference surface provided by the circumferential portion of the probe sheath indicated at 68. The heater 74 and its associated thermoelectric wire junctions are disposed internally of and circumferentially about the annular circumferential area 70 of the probe sheath that forms the test surface. The reference and test portions of the probe are mutually spaced by a distance sufficient to provide adequate thermal isolation between them. If deemed necessary or desirable, additional thermal isolation between reference and test surfaces may be provided.

The probe sheath has secured thereto a suitable fitting such as an externally threaded member 102 to cooperate with an internally threaded fitting 104 that is secured to a system (not shown in FIG. 6) containing fluid of which the foulant propensity is to be measured. Obviously, there are many other ways to mount the probe within a fluid system and such details form no part of the present invention. A specific but exemplary installation of this probe in a cooling water system will be described below.

Fixedly mounted to the outboard end of the probe is a housing 106 which includes certain electronic components such as pre-amplifier 108, a receptacle 110 for receipt of heating and measuring power cables, and a receptacle 112 for connection of the thermocouple leads and preamplifier leads to external circuitry to be described below.

It will be seen that the probe illustrated in FIGS. 6–9 provides all of the elements of the thermal bridge illustrated in FIG. 2 except for the meter, bridge and switches which are external to the probe and connected to its heater and thermocouple wires. The three (or more) thermocouple wires of one sleeve, such as wires 92a, 92b, 92c, are connected together within the housing 106 and similarly the three (or more) thermocouple wires 96a, 96b and 96c of the test surface sleeve are likewise connected together in the housing 106, thereby to provide two signals respectively individual to the test and reference surfaces, each signal denoting an average of the temperatures at circumferentially spaced points about the respective test and reference surfaces.

The described probe forms a thermal bridge of the type illustrated in FIG. 2. It provides a heat source in the form of heater coils 72, 74, a first heat path through the sleeve 82 and the test area 70 of the sheath 74 and a second heat path through the sleeve 80 and the reference surface area 68 of the sheath. Both the first and second heat paths are in contact with the mutually identical or very nearly identical fluid environments provided by flow of the same fluid past, over and about the probe in the direction of arrows 116.

ELECTRICAL CIRCUITS FOR THE PROBE

Various arrangements of circuits for the probe of FIGS. 6–9 are shown in FIGS. 10, 11, 12 and 13, illustrating only some of the different compensations, measurements and control that may be achieved. FIG. 10 shows an electrical circuit for use with the probe of FIGS. 6–9, including an adjustable compensation for thermal assymetry. The probe is shown schematically, including its sheath 64, reference surface 68, test surface 70, reference and test heaters 72, 74 and reference and test thermoelectric wire junctions 90 and 91, all of which schematically depict corresponding parts more specifically illustrated in FIGS. 6–9.

Heater power is derived from a source of electrical power (not shown) via a transformer 118 having a secondary winding 119 connected to an arm 120 of a dividing resistor 122 that has its ends connected to respective ones of a pair of ganged switches 124, 126. Switches 124 and 126 are connected via lines 128, 130 to opposite ends of heaters 72, 74 which themselves are connected together and have their common junction coupled to the other end of the secondary winding of transformer 18. Lines 128, 130 from the ends of the heater wires are also respectively connected to a pair of ganged switches 132, 134 which are respectively connected to a movable tap 136 and an end 138 of a secondary winding 139 of a transformer 140 that has its primary winding connected to a second source of electrical power (not shown).

The three thermocouple wires collectively represented in FIG. 9 by wire 96, are connected to each other at terminal 97 in a common isothermal junction box 142. Similarly, the three thermocouple wires collectively indicated by line 92 in FIG. 10 are connected to each other at terminal 99 in the junction box 142. Conventional copper wires 144, 146 connect these thermocouple terminals to the inputs of a differential amplifier 148.

Amplifier 148 provides an output signal proportional to the difference between the two averaged thermoelectrically generated voltages provided at the two inputs thereto, which difference may be represented as $\theta_t - \theta_r$ where $\theta_t$ is the temperature of the test surface and $\theta_r$ is the temperature of the reference surface.

A null adjusting or offset potentiometer 150 includes a variable resistance that is energized with potentials of opposite polarity and has its output added to the temperature difference signal from amplifier 148 in a resistive summing network 152, 154 of which the output is fed to a suitable indicating meter or other display, utilization or recording device 156.

Measuring current is provided to both of the heaters 72, 74 from the transformer 118 via the switches 124, 126, when closed, and foulant current, which heats only the test surface, is provided to heater coil 74 from transformer 140 when witches 132 and 134 are closed. Meter 156 reads the difference of temperatures sensed at the surfaces 68 and 70 during a measuring period.

PROBE ASYMMETRY COMPENSATION

Certain asymmetries exist in any real apparatus since it is not possible, as a practical matter, to make a probe having a test surface 68, sleeve 80, thermoelectric junction 90 and heater 72, all connected and operating thermally, physically and electrically, exactly the same as a second surface, such as test surface 70, sleeve 80, thermoelectric junction 91 and heater 74. Test and reference portions of the probe are asymmetrical despite the utmost care and effort exercised in an attempt to manufacture precisely identical reference and test elements. Such asymmetries between reference and test portions of the probe introduce variations of the meter reading (sensed temperature difference) during a measurement, which variations are caused by changes in the fluid environment. However, it is found that if the relative that inputs to the test and reference surfaces (in clean, unfouled condition) are varied, there will be a point in the relation between such heat inputs at which the measured temperature difference exhibits little or no variation over a significant range of variation of the fluid environment. It is postulated that, if the heating inputs to the two heaters are so varied as to achieve mutually equal temperatures at the test and reference surfaces (as distinguished from the thermoelectric junctions which are not precisely at the probe to fluid interface), changes in the fluid environment will not affect the difference in such temperatures. On the other hand, with equal heat inputs and asymmetry of thermal characteristics of the test and reference portions of the probe, temperature difference between the two surfaces will vary with variations in the fluid environment, partly because the heat paths to the fluid environment are not the same.

It is found that the described apparatus may be nulled or adjusted during an original measurement period, with both surfaces in clean and unfouled condition, by the following method. Switches 132, 134 are open. Switches 124, 126 are closed and the probe is immersed in a suitable fluid, which need not be the fluid of which foulant propensity is to be measured. An initial position of arm 120 of divider 122 is selected and the fluid environment is varied. For this adjustment fluid environment is most readily changed by varying fluid flow velocity past the probe, although one could also vary other characteristics of the fluid environment. Flow velocity is varied by any conventional means (not shown) such as an adjustable flow control valve. The temperature difference displayed by the meter 156 is observed as the fluid environment is varied. If the temperature difference varies as the fluid environment varies for a given position of arm 120, the arm is moved to change the relative heat inputs to the two heaters, and the fluid environment (fluid velocity) is again varied while observing measured temperature difference. A position of adjustment of arm 120 exists, and is found by this trail and error procedure, at which the reading of meter 156 does not fluctuate, or fluctuates only a minimum amount as fluid environment is varied. This position of adjustment of arm 120 to provide a selected relation of heat inputs to the two surfaces is then employed in all measurements made with this particular probe. As a practical matter, this adjustment may be made upon completion of manufacture of the probe, at the factory, and the relative heat input adjustment may then be fixed or built into the particular probe, being a characterized that is unique to each individual probe.

For example, having determined the adjusted relative heat inputs to the heaters of a given probe, according to the described procedure, fixed resistances may be employed in the heater circuits to provide this asymmetry compensation and variable divider 122 may be omitted.

Having unbalanced or adjusted the relative heat inputs, the temperature difference will not be zero, but the meter 156 may be made to read zero by varying the null adjust or offset potentiometer 150 to add or subtract from the signal $\theta_t - \theta_r$ at the output of difference amplifier 148 until the meter reading is zero. Now the probe and its circuitry have been compensated and adjusted to a null in a clean and unfouled condition of both surfaces. Switches 124 and 126 are opened and, with the probe (including both test and reference surfaces) immersed in a fluid of which the foulant propensity is to be measured, foulant switches 132 and 134 are closed to heat test surface 70 via heater 74 to a temperature controlled by adjustment of variable arm 136 of the secondary 138 of transformer 140. The temperature of the test surface 70 during the foulant period is selected to provide the temperature at which the desired monitoring and measuring of foulant propensity of the fluid is to be performed. If deemed necessary or desirable, temperature of the test surface may be measured during the foulant period by additional thermocouples or thermistors (not shown in FIG. 10) as described below. During the foulant period, reference surface 68 remains near the temperature of the ambient fluid flowing past the probe and thus it is not fouled during the foulant period, or if it is fouled, it is fouled to a considerably lesser degree. Of course, other differential fouling methods may be employed, as described herein.

After the fouling period, which may be one to four hours, for example, switches 132 and 134 are opened and switches 124 and 126 are again closed to apply the adjusted measuring heat. No further adjustments are made at this time. The reading of meter 156 is noted after the probe and its circuit have stabilized thermally. This stabilization period is needed at least in part because heat inputs to the test and reference surfaces have been changed. The reading of the meter, relative to the reading during the initial measuring period (which reading was adjusted to zero by means of offset potentiometer 150) is a measure of the heat transfer characteristics of test surface 70 with respect to the heat transfer characteristics of reference surface 68. The reading is independent of the substantially identical fluid environments in which the two surfaces are immersed, and is a measure of the foulant accumulated upon the test surface 70 during the foulant period, substantially independent of probe asymmetry.

In general, duration of the foulant period is chosen and the enhanced foulant condition of the test surface (as by increasing its temperature by means of heater 74) is chosen such that little or no foulant will normally occur on the reference surface 68 whereas there is a significantly greater probability that foulant will have been accumulated upon test surface 70. Many methods, including those set forth above, are available for ensuring a difference of foulant on test and reference surfaces during the foulant period. For example, prior to a foulant period, reference surface 68 may be provided with a protective sleeve. Alternatively, prior to the second measuring period, the probe may be removed and reference surface 68 cleaned of any possible foulant that might have been accumulated.

FLUID ENVIRONMENT COMPENSATION

The circuit illustrated in FIG. 10, when used with the probe of FIGS. 6-9, provides an instrument of high sensitivity and good reliability, compensated for certain probe asymmetries. Nevetheless, it is found that additional compensation of the null of a probe of high sensitivity will still further enhance such sensitivity. Even with the above described adjustment of relative heat inputs, changes in fluid environment of a probe of very high sensitivity may still cause a fluctuation of the reading of meter 156. Thus the described probe, although significantly better and more sensitive than prior art arrangements, will still exhibit an unwanted sensitivity to variations in fluid environment, when used in making high precision, high sensitivity measurement. It will be understood that high sensitivity to foulant is desirable in the described methods and apparatus because the earlier the detection of scale, and the smaller the amount of scale that can be detected, the greater the chance of taking corrective action before damage occurs.

Additional compensation for such fluid environment induced variations can be achieved to a significant extent in the manner illustrated in FIG. 11. In this arrangement compensation is provided by a signal representing the temperature difference between the reference surface and a third, differently heated (or unheated or indirectly heated) surface. In FIG. 11, a probe similar to the probe of FIGS. 6-9 is illustrated schematically. A probe sheath 160 has a reference surface 162, a test surface 164, a reference temperature sensing thermoelectric constantan to steel junction 166, a test temperature sensing thermoelectric constantan to steel junction 168 and reference and test heaters 170, 172, all connected and functioning as are the comparable elements of the probe described and illustrated in FIGS. 6-9. This probe, however, has an additional sensing thermoelectric junction 174 at a lesser (and indirectly) heated area 176 of the probe sheath 160, upstream from both test and reference surfaces. Operation and control of the heaters 170, 172 of this probe are the same as in the probe of FIGS. 6-9 and the circuit of FIG. 10, and therefore no discussion or illustration thereof is needed at this point. The reference and test surface junctions 166, 168 are connected to a differential amplifier 180 of which the output $\theta_t - \theta_4$ is combined in a resistive summing network 182 with a selectively variable offset derived from a potentiometer 184, just as in the previously described circuit.

In the arrangement of FIG. 11, however, the upstream area 176 of the probe sheath, which area may be termed a fluid environment area, has its temperature (relative to the reference surface temperature) sensed by a thermoelectric junction 174. The wires from both junctions 166 (reference surface sensor) and 174 are fed as the inputs to a second differential amplifier 186. Thus, $\theta_r$ designates the temperature at the reference surface and $\theta_a$ designates the sensed temperature at the "fluid environment" surface 176 (which is at a different temperature than the reference surface since the former is only indirectly heated and the latter is directly heated). Therefore, the output of amplifier 186 indicates the difference between these two differently heated surfaces, or $\theta_r - \theta_a$ which may be termed a "fluid environment" signal. A function of this "fluid environment" signal is employed in this compensation.

The fluid environment signal is fed to an inverting amplifier 188. The mutually opposite polarity outputs of amplifiers 186 and 188 are fed to opposite ends of a resistive divider 190, having a movable wiper arm 192. Wiper arm 192 is connected to provide one input to a resistive summing network 193 having a second input provided by an offset potentiometer 194 that provides a voltage of selectively variable magnitude and polarity picked off from a resistor 195 having its ends connected to sources of positive and negative potential. The output of summing network 193 is combined with the output of summing network 182 in a third summing network 196 and the output of the latter is fed to a meter 197 to provide a compensated reading of temperature difference between the test and reference surfaces.

The setting of potentiometer arm 192 for the fluid environment compensation is determined empirically, with the surfaces in clean, unfouled condition. With measuring power applied to the heaters and the probe immersed in a fluid that need not be the same as, but is preferably similar to, the fluid to be tested, the velocity of the passing fluid is significantly decreased from its normal, relatively constant measuring velocity. For example, one may normally measure with the described test probe at fluid velocities in the order of 100 centimeters per second. This velocity is decreased to half in this empirical determination and the change, if any, in the meter reading is noted. Then velocity is brought back to its normal measuring magnitude and the arm 192 is moved one way or another. Velocity is again dropped to the same degree as previously, to a 50 centimeters per second velocity, for example, and the variation of the meter caused by the velocity drop at this new position of arm 192 is noted. If such meter variation is greater than the previous variation, the arm 192 is moved in the other direction. If it is lesser, but still significant, the arm 192 is moved again, further, in the same direction. Once again velocity is brought back to its measuring condition, the meter reading is noted, arm 192 is moved in one direction or the other as indicated above, and the velocity again lowered. Once again the change in meter reading is noted and such change compared with the prior change in meter reading. This procedure is repeated until a point of adjustment of arm 192 is found at which significant variation of fluid velocity will cause little or no variation in meter reading. Now the probe has been further compensated for effects of fluid velocity variation upon the probe and this position of arm 192 is fixed, remaining constant throughout subsequent measuring. If deemed necessary, the new meter position with the empirically adjusted position of arm 192 is adjusted back to a zero reading by feeding into summing network 193 an offset adjustment signal from the offset potentiometer 194, or the potentiometer 184 may be used for this purpose and potentiometer 194 may be omitted.

For the empirical adjustment of resistive divider arm 192, the fluid environment is varied and the arm 192 is adjusted until a meter reading is attained that does not fluctuate as the fluid environment is varied. Actually, the empirical determination is obtained by varying a heat transfer characteristic of the fluid environment. However, as previously mentioned, one of such characteristics that is most readily varied is flow velocity. Thus, it is this specific fluid characteristic, flow velocity, that is varied in the empirical determination, although such determination may also be made by varying any other fluid environment characteristic that affects heat transfer characteristics of the fluid environment.

CONTROL OF FLUID ENVIRONMENT

The described thermal bridge provides greatly increased sensitivity which is further improved by the various circuits described herein for compensating for adverse effects of fluid environment. The bridge operation is also improved by use of precision electrical circuits and carefully regulated power supplies to eliminate still other sources of error. Nevertheless, a further improvement can still be made by a closed loop control and stabilization of the fluid environment. Thus, as also shown in FIG. 11, the fluid environment signal $\theta_r - \theta_a$, provided at the output of amplifier 186 during a measuring period, may be fed to a differential amplifier 198 having a second input in the form of an adjustable voltage set point derived from a potentiometer 199 that has its opposite sides energized with opposite polarity voltages. Amplifier 198 provides a feedback signal indicative of the sensed fluid environment ($\theta_r - \theta_a$) to operate a fluid environment adjustment controller 200 which controls a flow valve 201 that is opened greater or less amounts to increase or decrease fluid flow velocity in response to changes of sensed fluid environment. Obviously, the nature of the control of fluid environment can vary in many different ways. Thus, rather than adjust velocity in accordance with the output of amplifier 198, viscosity, temperature or other parameters that affect the heat transfer characteristics of the fluid environment may readily be adjusted in response to the sensed temperature difference between the heated reference surface 162 and the unheated surface 176 during the measuring period.

ADDITIONAL COMPENSATION

Figure 12:
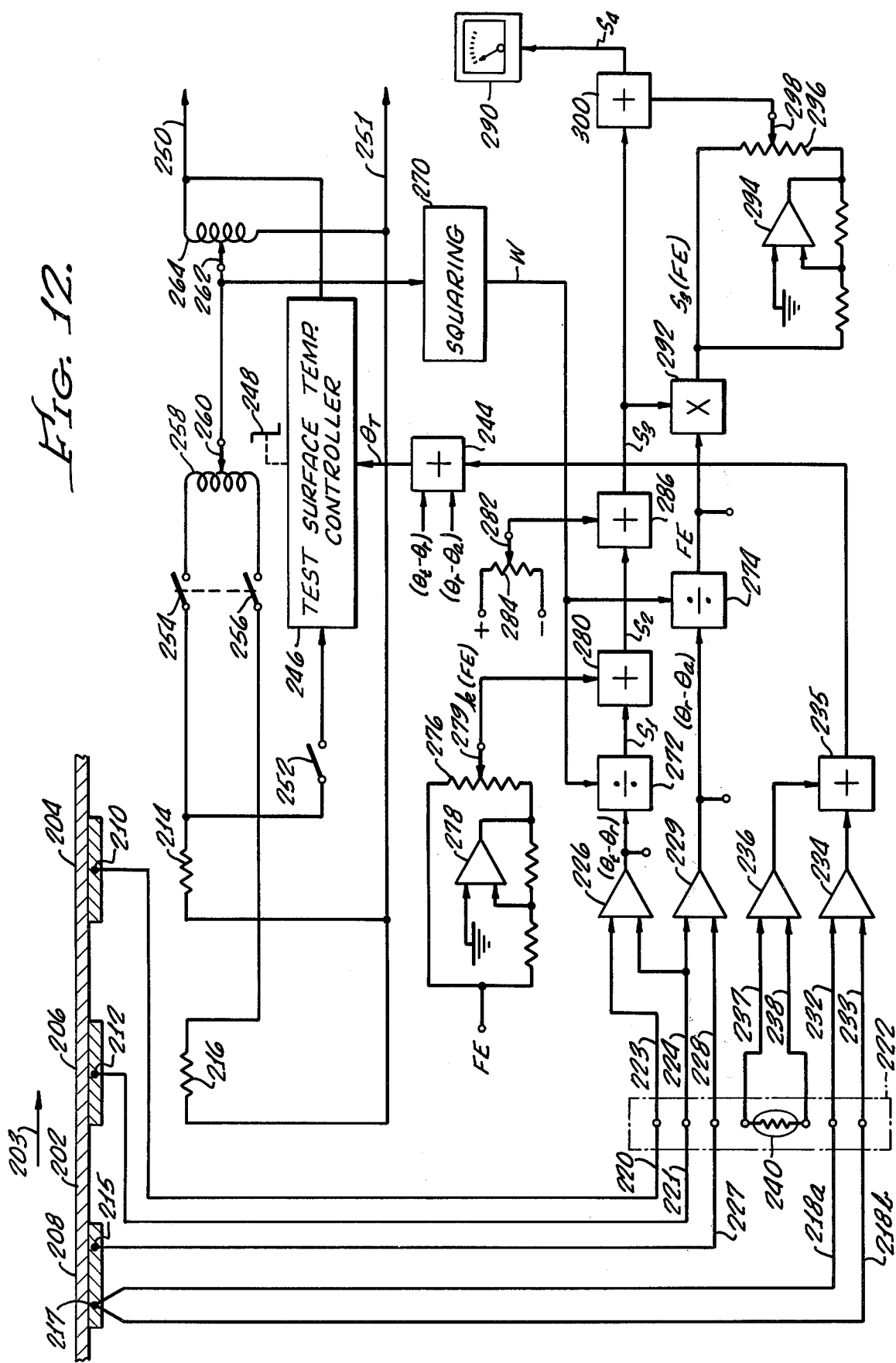
FIG. 12 shows still another modification of electrical circuits for use with the probe of FIGS. 6-9.

Although the above-described compensation and adjustment circuits will compensate for asymmetry of the probe and also further compensate the clean surface probe condition null adjustment for fluid environment variation, thereby to obtain even greater sensitivity in measurement and even greater decreased insensitivity to fluid environment variation, it is found that in scaled condition, with the test surface, for example, fouled to an amount sufficient to give a reading in the order of half full scale, meter readout is still subject to a fluctuation as fluid environment varies, even though foulant does not vary. Thus, at very high instrument sensitivities, variation of fluid environment during a measurement will cause a change in sensed temperature difference (as indicated on the meter) of the scaled or partially scaled probe. Compensation for this effect of fluid environment can be obtained. The effect of variation of fluid environment upon a scaled surface can be minimized, employing circuitry illustrated in FIG. 12. FIG. 12 shows substantially the same probe as previously described with certain modifications of its heating and measuring circuitry. This figure includes a showing of forms of both the previously described fluid environment compensations at null (using relative heat inputs and fluid environment sensing) and also shows circuitry for compensation of a fouled probe based upon the product of the foulant or scale reading ($\theta_t - \theta_4$) and a reading representing fluid environment ($\theta_r - \theta_a$).

In the arrangement of FIG. 12, fluid flows, as indicated by arrow 203, past a stainless steel probe sheath 202, having a test surface 204, a reference surface 206, and an upstream "fluid environment" surface 208. Thermoelectric junctions 210 and 212 are provided in spacer sleeves adjacent the test and reference surfaces respectively. Test and reference surface heaters 214, 216 are provided adjacent the test and reference surfaces as previously described. A third single constantan wire to steel thermoelectric junction 215 is provided at fluid environment surface 208 and a two-wire thermocouple junction 217 of chromel and alumel wires 218a, 218b is mounted adjacent surface 208 to provide an absolute measurement of temperature. Constantan wires 220 and 221 from junctions 210 and 212 respectively are connected at an isothermal junction box 222 to conventional electrical leads such as copper wires 223, 224 which provide inputs to a differential amplifier 226, having as its output the signal $\theta_t - \theta_r$ which is proportional to the difference in temperature at the test and reference surfaces. Line 221, connected to thermoelectric junction 212, together with a line 227 from thermoelectric junction 215, are connected at junction box 222 to copper wires 224, 228 which provide inputs to a second differential amplifier 229 having as its output the difference between temperatures at junctions 212 and 215, designated by the quantity $\theta_4 - \theta_a$. The absolute temperature at junction 217 is fed by thermocouple wires 218a, 218b via the junction box 222 for connection with copper wires 232, 233 as first and second inputs to an amplifier 234. The output of the latter is added in a summing network 235 to the output of an amplifier 236 which receives inputs on lines 237, 238 from a reference thermistor 240 employed to measure the temperature of the isothermal junction box 222 at which all of the thermocouple wires are connected to the conventional copper leads.

The output summing network 235 is a signal proportional to the absolute temperature at the "fluid environment" surface 208 and is combined in a summing network 244 with the output $\theta_t - \theta_r$ of amplifier 226 and the output $\theta_r - \theta_a$ of amplifier 229 which are fed to network 244 by leads (not shown). The summing network 244 provides a signal $\theta_T$ which represents the absolute temperature of test surface 204. This temperature of surface 204 is the sum of the temperature at surface 208 and the two temperature differences, between surfaces 208 and 206, and between 206 and 204. The signal from summing network 244 is compared in a test surface temperature controller 246 with a predetermined test surface temperature that is set into the controller 246 by means of a control knob 248. Controller 246 receives electrical power from lines 250, 251 and provides an output via a fouling period switch 252 to the test surface heater 214. Thus, during only the foulant period, power to the heater 214 is controlled in a closed loop arrangement and maintained at a temperature selected by control knob 248.

Measuring power is applied to both heaters 214 and 216 via ganged switches 254, 256 which are connected to respectively opposite ends of a coil 258 that is energized via a variable wiper arm 260 which, in turn, is connected to a wiper arm 262 of a coil 264 that is energized from input power lines 250 and 251.

Wiper arm 262 is adjusted to obtain the desired setting of or amount of measuring heat applied during the measuring period. Arm 260 is adjusted (in the manner and for the purpose described for adjustment of arm 120 of FIG. 10) to provide the selected relation of input heating power to the two heaters so as to compensate for probe asymmetry. Arm 260, as previously mentioned, can be adjusted and fixed in the factory during manufacture of the probe or its function provided by fixed resistances to attain the desired adjustment of relative heat inputs.

For highly precise measurements, comparably precise regulation of power supplies is required. However, to avoid expensive regulation of high power for heating purposes, temperature difference readings are compensated for voltage variations. The temperature difference signal $\theta_t - \theta_r$ is divided by a power signal W that is proportional to the square of heating voltage. Signal W is provided by a squaring circuit 270 having an input from arm 262 and an output to a divider 272 which also receives the temperature difference signal $\theta_t - \theta_r$ and divides the latter by W to provide the voltage compensated signal $S_1$.

Power signal W is also fed to a second divider 274 which receives the signal $\theta_r - \theta_a$ from amplifier 229 and which divides this signal by W to provide the voltage compensated fluid environment signal FE. Should the voltage input vary, the heat input to the test and reference surfaces will vary and an additional factor will be combined by dividers 272 and 274 with the temperature difference signals to compensate for the effects of such voltage variation.

A clean condition null adjustment for fluid environment is provided in the manner described in connection with voltage divider 190, 192 of FIG. 11. Thus the fluid environment signal FE from divider 274 is fed by leads (not shown) to one end of a resistor 276, inverted in amplifier 278, and fed to the other end of the resistor. Wiper arm 279 is adjusted as described in connection with the wiper arm 192 of FIG. 10 to attain minimum variation of the meter reading with variation of fluid environment. Thus a fluid environment compensation signal k(FE) from the arm 279 is added to the voltage compensated scale signal $S_1$ in a summing network 280 to provide a fluid environment compensated scale signal $S_2$.

An offset adjusting signal is derived from a movable arm 282 of a resistor 284 that has its opposite ends energized with positive and negative potentials. This offset adjusting signal is added to signal $S_2$ in summing network 286 to provide an adjusted scale signal $S_3$ which gives a zero reading of meter 290.

To compensate the adjusted scale signal $S_3$ for variations caused by fluid environment variations with the probe in a scaled condition, the fluid environment signal FE from divider 274 is multiplied in a multiplier 292 by the scale signal $S_3$ to provide the signal $S_3$(FE) for use as additional compensation. If there is no scale, $S_3$ is zero and this compensation is zero. The output of multiplier 292 is fed directly and also through an inverting amplifier 294 to opposite ends of a resistor 296 having a movable wiper arm 298. The signal on arm 298 is fed to a summing network 300 to be added to the scale signal $S_3$ at the output of offset summing network 286. The combined signal $S_4$ from summing network 300 is the final signal fed to meter 300, compensated for voltage variations, probe asymmetry, fluid environment variations that affect the probe in fouled condition, and fluid environment variations that affect the clean probe.

Arm 298 is empirically adjusted, in a manner substantially the same as the adjustment of arm 192 described in connection with FIG. 11 (and arm 279 of FIG. 12) but with the probe in a substantially fouled condition. Such fouled condition is equivalent, for example, to a condition that provides a half full scale reading of the meter. Arm 298 is initially placed in an intermediate position on resistor 296, the standard measuring heat is applied and velocity of fluid in which the probe is immersed is controlled to a preselected, normal measuring velocity. This velocity is then significantly decreased to a value of about one-half its original value, for example, and change, if any, in the meter reading is noted. Then the arm 298 is moved to a different position, the velocity brought back to normal and then again decreased. The fluctuation in meter reading caused by this change in velocity is again noted. If this fluctuation is less than the first noted fluctuation, the arm 298 has been moved in the proper direction. If the second fluctuation is greater, then the arm has been moved in the wrong direction. Thus, the arm 298 is again moved, the velocity brought back to normal and decreased, and a third fluctuation noted. This trial and error adjustment of the arm 298 continues until a position of the arm 298 is attained at which relatively large variation of velocity of the fluid environment will cause little or no change in the meter reading. Thus the arm 298 is now established at a position to compensate the meter readings of the scaled probe for possible fluctuations of the fluid environment. Thus still further insensitivity of the probe to fluid environment variations has been achieved.

It will be readily understood that the extent and accuracy of the empirical determinations of compensation by adjustment of arm 298, and also of arm 279 of FIG. 12 and arm 192 of FIG. 11, will depend upon the linearity of the effects of fluid environment variation with differing amounts of scaling on the test surface. The described compensation is linear and assumes a linear effect of fluid environment variation. Greater accuracy in this compensation may be achieved by empirically determining the form of the non-linearity (if any) of meter fluctuations with variations of the fluid environment and building such non-linearity into the signals applied to the divider resistors 296, 276 and 190.

In addition to the compensations provided by the circuit of FIG. 12, still further improvement in sensitivity and even greater reading stability can be achieved by closed loop control of fluid environment in the manner illustrated and described in connection with FIG. 11. Such control limits variation of fluid environment. Thus, the fluid environment signal FE may be employed as a feedback signal to control and minimize variation of specified parameters (such as velocity, viscosity, temperature, etc.) of the fluid environment, by feeding the FE signal to an amplifier and controller (not shown in FIG. 12) of the type shown in FIG. 11.

It will be seen that the described methods and apparatus require no measurement of temperature (as distinguished from temperature difference) or flow rates but provide improved foulant measurement and increased sensitivity by several different features and compensations. First, use of the described thermal bridge affords a major primary improvement in independence of fluid environment. Second, adjusted relative heat inputs compensate for thermal asymmetry. Third, fluid environment compensation is provided for null adjustment. Fourth, a combined scale and fluid environment compensation is provided for fouled condition. Fifth, closed loop control of fluid environment is provided. Each of the second through fifth features can be used alone or in conjunction with one or more of the others to enhance operation of the described thermal bridge.

The readout meters can be calibrated in degrees of temperature difference, or, by dividing the temperature difference by the measurement period heat flux density in watts per square centimeter, the meter may be calibrated to read degrees centimeter squared per watt (deg.cm$^2$/watt), units of thermal resistivity.

Although the probes of FIGS. 6–12 have the reference surface upstream of the test surface, it will be readily appreciated that these positions may be reversed. Such reversed position is particularly desirable where additional temperature sensing areas are employed, as in FIG. 12. Thus for a probe of the type shown in FIG. 12, the test area 204 (and associated heating sensing elements) could be positioned at the upstream end of the probe, the fluid environment area 208 at the downstream end (near the probe head from which the wires exit), and the reference area would remain between the two. Such an arrangement avoids the need to pass wires from reference and fluid environment areas through the region of test surface heating.

MEASUREMENT OF HEAT FLUXES

The embodiments described heretofore compare heat transfer characteristics of the first and second path of the thermal bridge by detecting the temperature difference at or adjacent the test and reference surfaces. It will be readily appreciated that this thermal bridge measurement also may be made by measuring differences in heat flux needed to maintain equal temperatures at the test and reference surfaces. Portions of the circuit of FIG. 12 modified to provide such control of input heat fluxes are shown in FIG. 13 wherein parts common to the circuit of FIG. 12 are designated by the same reference numbers. Thus, measuring heating power is fed via movable arm 260, coil 258 and ganged switches 254 and 256 to the respective heaters 214 and 216. In this embodiment arm 260 is driven by a motor 310 which is operated in one direction or another from an amplifier 312, having a first input from amplifier 226 (see also FIG. 12) which provides a signal representing the temperature difference $\theta_t - \theta_r$ as shown in FIG. 12. Amplifier 312 may have a second input from an offset potentiometer 314 having a resistive divider energized at its opposite sides with plus and minus voltages.

The signal $\theta_t - \theta_r$ representing the temperature difference between reference and test surfaces, is balanced by potentiometer 314 which is adjusted to provide a null output from amplifier 312 when the two surfaces are at equal temperatures. Should the balanced temperature difference vary from zero, a signal is fed to motor 310 to change the heat input of heaters 214 and 216 by varying the position of arm 260 in such a direction as to maintain a fixed or zero temperature difference. The angular displacement of the output shaft of motor 310 indicates the difference in heat flux required to maintain equal temperatures at test and reference surfaces and, therefore, is a measure of foulant on the test surface. This shaft displacement is caused to operate a meter or other output device 316 to display, record or utilize the foulant measure. When measuring heat flux difference, the several compensations for fluid environment variations and for probe asymmetry, as shown in FIG. 12, are not employed. Other forms of compensations (not shown) may be provided if deemed necessary or desirable.

TYPICAL PROBE APPLICATION

As previously mentioned, the methods and apparatus described herein are useful in many different types of systems. Nevertheless, for purposes of exposition, FIG. 14 illustrates application of the probe of FIGS. 6–9 to a particular system, a cooling water system 340, of which the scaling or foulant propensity is to be monitored. For such typical application of the present probe, water from the cooling system is drawn off through a conduit 342 and heated as it flows through a heater 344 to raise its temperature to a value at which its foulant propensity is to be measured. This temperature may be, for example, the temperature of cooling water adjacent a surface of heat exchanger elements that are in contact with and cooled by the cooling water being monitored by the probe. It is generally at such hot heat exchanger surfaces that foulant coatings are heaviest. The heated water from the system flows through a diverter valve 346, and thence, via a conduit 348, to a conduit 352. The heated water from the cooling system flows via the long straight conduit 352 through a tee fitting 354 having one arm connected to conduit 352. The tee fitting has an output arm 356 connected to discharge water flowing from conduit 352 into a sump 358 from which it may be either discharged from the system or returned to the system, if desired. The other end of the tee is arranged to receive a probe such as the probe illustrated in FIGS. 6–9, having its sheath inserted through the tee into the long straight section 352 of pipe between the tee and the valve 346. Probe housing 106 (see also FIG. 6) is detachably connected to and protrudes from the free end of the tee. The entire probe may be inserted into and removed from the fluid system by means of this connection.

Valve 346 is also connected to a source 360 of fresh water, such as tap water, and is operable between a first (foulant) position in which it will flow water from heater 344 to conduit 348 while blocking flow of fresh water from source 360, and a second (measuring) position in which water will flow from fresh water source 360 to conduit 348, while flow from heater 344 is blocked.

The probe is inserted in the tee with valve 346 in its measuring position to block flow from heater 344 and to provide a flow of relatively cool water from fresh water system 360. The several null and compensation adjustments of the probe, as described above in connection with FIG. 12, are carried out during an initial measuring period with the two probe heaters energized with a chosen measuring heat to provide a reference and test surface temperature higher than the temperature of ambient fluid. After this initial adjustment in the measuring period, valve 346 is operated to its foulant position to cut off the flow of cool fresh water and to pass water from heater 344 to the probe. The heater 344 is set to provide the desired temperature of the monitored water from the cooling system, the temperature at which foulant propensity is to be measured. This heated water flows past the probe, which is now in its foulant period, and to the sump. In the foulant period of the probe, measuring heat is removed from the heaters and only the test surface heater is energized, all as described in connection with FIGS. 10, 11 or 12. This foulant period, as previously mentioned, may have a duration of from one to several hours. At the end of this period the probe circuit is switched back to a measuring condition. The foulant heating power is removed, measuring power is applied to heat both reference and test surfaces, and valve 346 is once again operated to shut off flow from the cooling water system and to provide fresh water at the temperature of source 360 (which may be in the order of 60° F. to 70° F.) over the probe and into sump 356. This cyclical switching between foulant and measuring condition, switching the probe heater circuits and the valve 346 may be performed manually. However, for long term operation, an automic timing controller (not shown) may be employed for these simple repetitive switching functions.

With the probe again in its measuring condition, a second measurement is made and the reading of a meter or recorder 360, connected to the probe circuit to display or record foulant measurement, provides an indication of the foulant propensity of the cooling water system. It is to be noted, that, in the illustrated application, the probe operates in the fluid that is being monitored (water of cooling system 340) only during the foulant periods, whereas during the measuring periods, another fluid, such as tap water, is employed. The tap water is cooler than the heated water from the cooling water system 340 and thus a greater heat flow across the test and reference surfaces can be provided to afford an increased sensitivity. The measuring period fluid may be chosen to have other characteristics that are desirable for the measuring period. The desired lower fluid temperature during measuring may be provided, alternatively, merely by de-energizing heater 344, without using a second source of fluid, in which case valve 346 may be omitted.

As previously noted, the described methods and apparatus for employing differential thermal measurements to detect and monitor scale can be carried out in a great many modified forms and by means of a large number of different configurations of apparatus. Some of the different methods of heating the surfaces to effect a differential fouling, different methods of differential fouling, and methods and apparatus for sensing temperature and/or heat flux have been described. The described methods and apparatus are primarily adapted for detection, measuring and monitoring of foulant or potentially foulant conditions in a fluid system. At present it is contemplated that a probe such as that shown in FIGS. 6–9 will be permanently installed in a system to be monitored and provided with automatic timing and control mechanism that will continuously and repetitively cycle the apparatus through the described steps, automatically causing the apparatus to go through alternate measuring and foulant cycles, recording each measurement. In such an automatic system, a measurement will be made as often as every one or two hours so that a large number of measurements can be made and averaged in order to better determine any change in the measurement. Such change will signal a change in foulant propensity of the fluid system under observation.

In many systems, foulant is slow to build up and harmful effects may occur only over long periods of time. Nevertheless, the described invention can be employed to achieve effective monitoring or foulant propensity over such long periods of time and, long before damaging foulant build up, will detect such changes in measured foulant propensity as might be considered sufficient to warrant corrective action. Detected changes in foulant propensity may be employed in a control system which automatically provides an alarm and, in addition, which takes appropriate and sufficiently early corrective action such as automatically adding additional inhibitor to the system.

To further compensate for deviations of fluid environment between the test and reference surfaces during a test, the probe may be built with two reference surfaces positioned symmetrically at equal axial distances upstream and downstream respectively from the test surface. The heating powers to the two reference surfaces are equal and the measured temperatures of the two reference surfaces are averaged so as to compensate for possible axial asymmetry in fluid environment and to compensate for possible axial gradient of fluid temperature.

One type of application of the described invention measures foulant accumulation on cooled surfaces. In such application, during only the measuring period, the reference and test surfaces are cooled instead of being heated. The fluid environment may be a hot geothermal fluid, whereby heat flows from the fluid environment to the cooled test and reference surfaces.

It will be noted that reversing the direction of heat flow (for a cooled surface application) in the thermal bridge of FIG. 2 (making box 18 a heat sink and box 28 a heat source), will not alter any of the thermal bridge characteristics, any more than voltage polarity reversal on an electrical bridge changes its principle of operation.

The foregoing detailed description is to be clearly understood as given by way of illustration and example only, the spirit and scope of this invention being limited solely by the appended claims.

What is claimed is:

1. A method of testing a fluid environment for a propensity to deposit foulant upon a surface immersed therein comprising,
    subjecting a test surface to said fluid environment whereby foulant may be deposited thereon, subjecting both a reference surface and said test surface to fluid environments having a known relation of heat flow parameters,
    subjecting said reference surface to said first mentioned fluid environment during said first mentioned step,
    varying the propensity of said first mentioned fluid environment to deposit foulant upon said test surface relative to its propensity to deposit foulant upon said reference surface during said first mentiond step,
    transferring heat between said surfaces and their respective fluid environments, and
    comparing the heat transfer characteristics of said surfaces adjacent their respective fluid environments.

2. The method of claim 1 including the step of causing said surfaces to have a predetermined relation of thermal characteristics prior to said first mentioned step, and wherein said step of comparing comprises comparing thermal characteristics of said surfaces to thereby determine whether or not said test surface thermal characteristic has changed because of foulant deposited thereon by said first mentioned fluid environment.

3. The method of claim 3 wherein said surfaces are caused to have substantially the same thermal characteristics prior to said first mentioned step.

4. The method of claim 1 wherein said step of comparing comprises applying thermal fluxes to said test and reference surfaces, and comparing the temperatures of said surfaces.

5. The method of claim 1 wherein said step of varying includes the step of protecting said reference surface from deposit of foulant thereon by said first mentioned fluid environment during said first mentioned step.

6. A method of testing a fluid environment for a propensity to deposit foulant upon a surface immersed therein comprising, subjecting a test surface of said fluid environment whereby foulant may be deposited thereon, subjecting both a reference surface and said test surface to fluid environments having a known relation of heat flow parameters, comparing the heat transfers between said surfaces and their respective fluid environments, said step of comparing including sensing the difference in temperature of said test and reference surfaces, and applying to said surfaces respectively first and second heat fluxes differentially adjusted to decrease variation of said difference in temperature with variation of the fluid environments to which said test and reference surfaces are subjected.

7. A method of testing a fluid environment for a propensity to deposit foulant upon a surface immersed therein comprising, subjecting a test surface to said fluid environment whereby foulant may be deposited thereon, subjecting both a reference surface and said test surface to fluid environments having a known relation of heat fluid parameters, comparing the heat transfers between said surfaces and their respective fluid environments, said step of comparing comprising applying thermal fluxes to said test and reference surfaces, comparing the temperatures of said surfaces, and including the step of differentially adjusting the thermal fluxes applied to said test and reference surfaces so as to decrease variation of the temperature comparison with variation of the fluid environments to which said surfaces are both subjected.

8. A method of testing a fluid environment for a propensity to deposit foulant upon a surface immersed therein comprising, subjecting a test surface to said fluid environment whereby foulant may be deposited thereon, subjecting both a reference surface and said test surface to fluid environments having a known relation of heat flow parameters, comparing the heat transfers between said surfaces and their respective fluid environments, said step of comparing comprising applying mutually different thermal fluxes to said test and reference surfaces to maintain mutually equal temperatures at said surfaces, and comparing the respective thermal fluxes applied to said surfaces respectively.

9. A method of testing a fluid environment for a propensity to deposit foulant upon a surface immersed therein comprising, subjecting a test surface to said fluid environment whereby foulant may be deposited thereon, subjecting both a reference surface and said test surface to fluid environments having a known relation of heat flow parameters, comparing the heat transfers between said surfaces and their respective fluid environments, subjecting said reference surface to said first mentioned fluid environment during said first mentioned step, and varying the propensity of said first mentioned fluid environment to deposit foulant upon said test surface relative to its propensity to deposit foulant upon said reference surface during said first mentioned step.

10. The method of claim 9 wherein said step of varying propensity to deposit foulant comprises providing different temperatures at said test and reference surfaces 11. A method of testing a fluid environment for a propensity to deposit foulant upon a surface immersed therein comprising, subjecting a test surface to said fluid environment whereby foulant may be deposited thereon, subjecting both a reference surface and said test surface to fluid environments having a known relation of heat flow parameters, and comparing the heat transfers between said surfaces and their respective fluid environments, said last mentioned fluid environments being substantially identical to each other and being different than said first mentioned fluid environment.

12. A method of testing a fluid environment for a propensity to deposit foulant upon a surface immersed therein comprising, subjecting a test surface to said fluid environment whereby foulant may be deposited thereon, subjecting both a reference surface and said test surface to fluid environments having a known relation of heat flow parameters, and comparing the heat transfers between said surfaces and their respective fluid environments, including the step of applying a first thermal flux to said test surface during said first mentioned step to enhance the propensity to deposit foulant and applying second thermal fluxes to both said test and reference surfaces during said step of comparing.

13. A method of testing a fluid environment for a propensity to deposit foulant upon a surface immersed therein comprising, subjecting a test surface to said fluid environment whereby foulant may be deposited thereon, subjecting both a reference surface and said test surface to fluid environments having a known relation of heat flow parameters, and comparing the heat transfers between said surfaces and their respective fluid environments, including the step of varying the foulant forming conditons present at the interface between said test surface and said fluid environment to thereby change the rate of foulant deposited upon said test surface, said last mentioned step being carried out prior to said step of comparing.

14. A method of testing a fluid environment for a propensity to deposit foulant upon a surface immersed therein comprising, subjecting a test surface to said fluid environment whereby foulant may be deposited thereon, subjecting both a reference surface and said test surface to fluid environments having a known relation of heat flow parameters, transferring heat between each said surface and its respective fluid environment, sensing the difference in temperatures of said surfaces, sensing a heat transfer characteristic of said last mentioned fluid environments, and compensating said sensed difference in temperature in accordance with said sensed heat transfer characteristic.

15. The method of claim 14 wherein said step of compensating comprises combining with said sensed difference in temperature a quantity that is a function of the product of a first quantity representing said sensed temperature difference and a second quantity representing said sensed heat transfer characteristic.

16. The method of detecting deposition of adherent precipitate upon a surface which comprises:
    providing first and second surfaces,
    exposing said surfaces to a fluid which may deposit an adherent precipitate thereon,
    varying the propensity of said first mentioned fluid environment to deposit foulant upon said test surface relative to its propensity to deposit foulant upon said reference surface during said second mentioned step,
    exposing said surfaces to fluid environments having a known relation of heat flow parameters,
    enhancing heat flow between said surfaces and said fluid environments, and
    comparing heat transfer characteristics of said first and second surfaces adjacent said fluid environments having a known relation of heat flow parameters.

17. The method of detecting deposition of adherent precipitate upon a surface which comprises:
    providing first and second surfaces,
    exposing said surfaces to a fluid which may deposit an adherent precipitate thereon,
    enhancing the deposition rate on said first surface with respect to the deposition rate on said second surface to thereby induce more deposition of adherent precipitate on said first surface than on said second surface, and
    comparing heat transfer of said first and second surfaces to fluid environments having a known relation of heat flow parameters, said step of enhancing comprising providing different temperatures at said first and second surfaces.

18. The method of detecting deposition of ahderent precipitate upon a surface which comprises:
    providing first and second surfaces,
    exposing said surfaces to a fluid which may deposit an adherent precipitate thereon,
    enhancing the deposition rate on said first surface with respect to the deposition rate on said second surface to thereby induce more deposition of adherent precipitate on said first surface than on said second surface,
    comparing heat transfer characteristics of said first and second surfaces, and
    providing heat inputs to said first and second surfaces relatively adjusted to unbalance temperature difference at said surfaces in a sense to decrease sensitivity to changes in fluid environment.

19. The method of monitoring foulant accumulation upon a surface that has been exposed to a fluid that may be foulant comprising:
    exposing said surface and a reference surface to a common fluid,
    comparing the heat transfer between said common fluid and each said surface, and
    compensating for initial differences in thermal transfer characteristics of said surfaces by applying compensatory differential heating thereto when said surfaces are in mutually similar conditions of surface accumulations.

20. The method of monitoring foulant accumulation upon a surface that has been exposed to a fluid that may be foulant comprising:
    exposing said surface and a reference surface to a common fluid,
    comparing the heat transfer between said common fluid and each said surface, and
    compensating said comparing of heat transfer according to variation of heat transfer characteristics of said common fluid.

21. The method of monitoring foulant accumulation upon a surface that has been exposed to a fluid that may be foulant comprising:
    exposing said surface and a reference surface to a common fluid,
    comparing said heat transfer between said common fluid and each said surface, and
    controlling said common fluid according to variations of its heat transfer characteristics, thereby to decrease said variations.

22. A foulant probe comprising:
    first and second surfaces,
    means for heating said surfaces,
    means for measuring temperature of said surfaces,
    a probe sheath having first and second areas thereof forming said test and reference surfaces respectively,
    said means for heating comprising a heater having first and second heater portions mounted within said sheath and positioned at said first and second areas respectively,
    said means for measuring temperature comprising first and second sleeves interposed between each of said heater portions and said first and second areas respectively, and
    first and second heat sensing elements connected with said first and second sleeves adjacent said first and second sheath areas respectively.

23. The probe of claim 22 wherein at least one of said heat sensing elements is a thermoelectric wire joined to one of said sleeves, said wire and at least one of said sleeve and sheath being formed of different materials that generate an electrical signal indicative of the temperature of the junction thereof.

24. The probe of claim 23 wherein each of said sleeves is formed with a longitudinally extending groove and said thermoelectric wires lie in said grooves.

25. The probe of claim 23 wherein said sheath is formed with an aperture, and including a material having a low thermal resistivity in said aperture and between at least parts of said sheath and one of said sleeves to provide a low thermal resistivity path from said sleeve to the exterior of said sheath.

26. A thermally sensitive foulant probe comprising
    an elongated cartridge having first and second heater elements mounted thereto at first and second areas thereof spaced axially along said cartridge,
    a first sleeve circumscribing said cartridge in close thermal contact with said first area thereof,
    a second sleeve circumscribing said cartridge in close thermal contact with said area second thereof,
    an elongated probe sheath circumscribing said cartridge and said sleeves in close thermal contact with said sleeves, and
    first and second temperature sensing devices fixed to and between said probe sheath and said first and second sleeves respectively.

27. The probe of claim 26 wherein said temperature sensing devices are thermoelectric wires.

28. The probe of claim 26 including means for forming a wire receiving conduit between said sheath and at least one of said sleeves, and at least one of said wires of one of said sensing devices extending from the other of said sleeves through said conduit.

29. The probe of claim 26 wherein at least one of said sleeves is formed with a plurality of longitudinally extending slots on the exterior surface thereof, a plurality of wires extending through some of said slots between said sleeve and said sheath and having their ends connected to said sleeve, the other of said sleeves having a plurality of longitudinally extending slots formed in an exterior surface thereof, said plurality of wires extending through some of the slots in said second sleeve between the sleeve and said sheath.

30. The probe of claim 26 wherein at least one of said sensing devices is a thermoelectric junction formed by a single thermoelectric wire and said sleeve and sheath.

31. A foulant probe adapted to be immersed in a fluid environment of which the foulant propensity is to be measured, said probe comprising:
first and second measuring surfaces,
means for heating said surfaces,
means for measuring the temperature of said surfaces to generate a measurement signal,
a source of heater power,
means for applying said power to said heating means, and
means for compensating said measurement signal in accordance with variations of said heater power.

32. A foulant probe adapted to be immersed in a fluid environment of which the foulant propensity is to be measured, said probe comprising:
first and second measuring surfaces,
means for heating said surfaces,
means for measuring the temperature of said surfaces to generate a measurement signal,
said heating means comprising means for providing relative heating to said surfaces in a predetermined relation that yields a decreased change in difference between said temperatures for changes in said fluid environment.

33. The probe of claim 32 including means for compensating said measurement signal for changes in said fluid environment when said surfaces are in like condition.

34. The probe of claim 32 including means for compensating said measurement signal for changes in fluid environment when said surfaces are in different conditions.

35. A foulant probe adapted to be immersed in a fluid environment of which the foulant propensity is to be measured, said probe comprising:
first and second measuring surfaces,
means for heating said surfaces,
means for measuring the temperature of said surfaces to generate a measurement signal, and
means responsive to said fluid environment for compensating said measurement signal in accordance with a characteristic of said fluid environment, said characteristic of said fluid environment being one of the characteristics of viscosity and flow velocity.

36. A foulant probe adapted to be immersed in a fluid environment of which the foulant propensity is to be measured, said probe comprising:
first and second measuring surfaces,
means for heating said surfaces,
means for measuring the temperature of said surfaces to generate a measurement signal,
means responsive to said fluid environment for compensating said measurement signal in accordance with a characteristic of said fluid environment,
said means for compensating said measurement signal comprising means for sensing a characteristic of said fluid environment that varies its thermal effect upon said test and reference surfaces,
means responsive to said last named sensing means for generating a fluid environment signal, and
means for adding said fluid environment signal to said measurement signal.

37. A foulant probe adapted to be immersed in a fluid environment of which the foulant propensity is to be measured, said probe comprising:
first and second measuring surfaces,
means for heating said surfaces,
means for measuring the temperature of said surfaces to generate a measurement signal,
means responsive to said fluid environment for compensating said measurement signal in accordance with a characteristic of said fluid environment,
said means for compensating comprising means for sensing a characteristic of said fluid environment that varies its thermal effect upon said test and reference surfaces, means responsive to said last named sensing means for generating a fluid environment signal representative of changes in said fluid environment,
means for combining said measurement signal with said fluid environment signal,
means for generating a compensation signal that is a function of said combined measurement and fluid environment signal, and
means for combining said compensation signal with said measurement signal to provide an indication of foulant on said test surface as compared to said reference surface, said indication being compensated for variation of said fluid environment.

38. A foulant probe adapted to be immersed in a fluid environment of which the foulant propensity is to be measured, said probe comprising:
first and second measuring surfaces,
means for heating said surfaces,
means for measuring the temperature of said surfaces to generate a measurement signal that indicates foulant propensity, and
including means responsive to said fluid environment for varying said fluid environment to decrease variation of a heat flow parameter thereof.

39. The method of monitoring foulant propensity of fluid of a fluid system comprising the steps of
flowing fluid from said system over reference and test surfaces,
enhancing the propensity of said fluid to deposit foulant upon said test surface during a foulant period,
flowing fluids having a known relation of heat flow parameters over said test and reference surfaces respectively during a measuring period,
applying heat flux to both said surfaces during said measurement period to enhance transfer of heat therefrom to said fluids, and
measuring transfer of heat from said test and reference surfaces to said fluids during said measuring period.

40. The method of claim 39 wherein said step of flowing fluid during a measuring period comprises flowing fluid of a temperature lower than the temperature of fluid flowing during said foulant period.

41. The method of claim 39 wherein said step of flowing fluid during a measuring period comprises flowing fluid from a source other than said fluid system.

42. The method of claim 41 including the step of heating fluid from said system before flowing such fluid over said surfaces during said foulant period.

43. The method of claim 39 including heating said test and reference surfaces during said measuring period and wherein said step of measuring temperature comprises measuring the temperature of said test surface with respect to the temperature of said reference surface.

44. A thermal probe adapted to be immersed in a fluid environment to detect foulant propensity thereof, said probe comprising
- test, fluid environment, and reference surfaces, test and reference heaters adjacent said test and reference surfaces respectively,
- means for differentially measuring temperature at said test and reference surfaces, and
- means responsive to temperature of said fluid environment surface for compensating the differentially measured temperature of said test and reference surfaces.

45. A thermal probe adapted to be immersed in a fluid environment to detect foulant propensity thereof, said probe comprising:
- test and reference surfaces,
- test and reference heaters adjacent said test and reference surfaces respectively,
- means for differentially measuring temperature at said test and reference surfaces,
- means for providing heating power to said heaters, and
- means for effecting a difference in the heating power applied to said heaters to compensate for differences in thermal characteristics of the heat path including said reference surface and its associated heater and the heat path including said test surface and its associated heater.

46. A thermal probe adapted to be immersed in a fluid environment to detect foulant propensity thereof, said probe comprising:
- test and reference surfaces,
- test and reference heaters adjacent said test and reference surfaces respectively,
- means for differentially measuring temperature at said test and reference surfaces,
- said surfaces comprising first and second portions of a probe body of thermoelectric material,
- said means for differentially measuring temperature comprising a first wire joined to said first probe body portion,
- a second wire connected to said second probe body portion, said wires being formed of a thermoelectric material different than the material of said probe body, and
- means for measuring the voltage difference between said wires at points thereof remote from their respective junctions with said probe body to thereby measure the temperature difference between said junctions.

47. A foulant probe adapted to be immersed in a fluid environment of which the foulant propensity is to measured, said probe comprising:
- first and second measuring surfaces,
- means for heating said surfaces,
- means for differentially measuring the temperature of said surfaces to generate a measurement signal, and
- means responsive to said fluid environment for compensating said measurement signal in accordance with a characteristic of said fluid environment.

48. A method of testing a fluid environment for a propensity to deposit foulant upon a surface immersed therein comprising:
- subjecting a test surface to said fluid environment whereby foulant may be deposited thereon,
- subjecting both a reference surface and said test surface to fluid environments having a known relation of heat flow parameters,
- comparing the heat transfers between said surfaces and their respective fluid environments,
- sensing a heat transfer characteristic of said last mentioned fluid environments, and
- compensating said comparison of heat transfers in accordance with said sensed characteristic.

49. A thermally sensitive foulant probe comprising
- an elongated probe sheath,
- first and second heater elements spaced axially along said sheath,
- a first sleeve circumscribing said first heater element in close thermal contact therewith,
- a second sleve circumscribing said second heater element in close thermal contact therewith, said elongated probe sheath circumscribing said heater elements and said sleeves in close thermal contact with said sleeves, and
- first and second temperature sensing devices fixed to said first and second sleeves respectively adjacent said sheath.

* * * * *